US012168052B2

(12) United States Patent
Soon-Shiong

(10) Patent No.: US 12,168,052 B2
(45) **Date of Patent: *Dec. 17, 2024**

(54) NANT COVID VACCINE CROSS REACTIVITY

(71) Applicant: ImmunityBio, Inc., Culver City, CA (US)

(72) Inventor: Patrick Soon-Shiong, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/620,192

(22) Filed: Mar. 28, 2024

(65) Prior Publication Data

US 2024/0226282 A1 Jul. 11, 2024

Related U.S. Application Data

(63) Continuation of application No. 18/533,042, filed on Dec. 7, 2023, now Pat. No. 12,016,916, which is a continuation of application No. 18/060,513, filed on Nov. 30, 2022, now Pat. No. 11,911,459.

(60) Provisional application No. 63/284,203, filed on Nov. 30, 2021.

(51) Int. Cl.

| | |
|---|---|
| ***A61K 39/215*** | (2006.01) |
| ***A61K 39/00*** | (2006.01) |
| ***A61P 31/14*** | (2006.01) |

(52) U.S. Cl.

CPC ............ *A61K 39/215* (2013.01); *A61P 31/14* (2018.01); *A61K 2039/545* (2013.01); *A61K 2039/572* (2013.01)

(58) Field of Classification Search

CPC .. A61K 39/215; A61K 2039/545; A61P 31/14

See application file for complete search history.

(56) References Cited

U.S. PATENT DOCUMENTS

2023/0256083 A1* 8/2023 Sahu .................. C07K 14/1808 424/186.1

OTHER PUBLICATIONS

Bangaru et al. Structural analysis of full-length SARS-CoV-2 spike protein from an advanced vaccine candidate. Science. Nov. 27, 2020;370(6520):1089-1094. (Year: 2020).*

* cited by examiner

*Primary Examiner* — Janet L Andres
*Assistant Examiner* — Ruixue Wang
(74) *Attorney, Agent, or Firm* — Umberg Zipser LLP

(57) ABSTRACT

Recombinant SARS-CoV2 vaccine compositions and methods are presented that have unexpected cross-reactivity against a variety of other coronaviruses, and particularly against SARS-CoV1, MERS-CoV, OC43-CoV, and HKU1-CoV in addition to significant reactivity against SARS-CoV2A. Moreover, the vaccine compositions presented herein also produced cross-reactive memory B cells as well as cross-reactive memory T cells with cross-reactivity spanning a relatively wide range of different coronaviruses.

16 Claims, 14 Drawing Sheets

Specification includes a Sequence Listing.

NANT COVID VACCINE CROSS REACTIVITY

This application is a continuation of co-pending U.S. application Ser. No. 18/533,042, filed Dec. 7, 2023, which is a continuation of U.S. Pat. No. 11,911,459, filed Nov. 30, 2022, which claims the benefit of the U.S. provisional application 63/284,203, filed Nov. 30, 2021. Each of these applications are incorporated by reference herein in its entirety.

SEQUENCE LISTING XML

The content of the following file which was electronically submitted via EFS-Web along with the present application is incorporated by reference herein in its entirety: a computer readable form (CRF) of the Sequence Listing, file name: Seq_List_102538.0086US3.xml, created on Mar. 27, 2024, and having the size 61.8 KB.

FIELD OF THE INVENTION

The field of the invention is vaccine composition and methods, especially as it relates to cross-reactive vaccine compositions that are effective for a variety of corona viruses.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

While SARS-CoV2 diagnostic tests have become available in relatively short time, numerous attempts to treat the disease have so far shown mixed or inconclusive results. Most typically, patients with severe symptoms are treated to maintain respiration/blood oxygenation. More recently, use of vaccination efforts and antibody cocktails (e.g., casirivimab and imdevimab) as well as newly developed antiviral agents such as paxlovid (Pfizer) or molnupiravir (Merck) have reduced the rate hospitalization and mortality. Nevertheless, the COVID19 mortality rate remained significant, particularly in elderly, immune compromised individuals, and individuals with heart disease, lung disease, or diabetes. Despite improvements in acute care, it has become apparent that containment of the disease is critically important as social distancing and other public health mitigation measures can provide only moderate relief. Such need for containment is particularly pressing as new virus mutants are bound to evolve over time, and it is anticipated that at least some of these mutants may escape currently known immune therapies.

Moreover, as can be seen from FIG. 1, protection of the recently introduced SARS-CoV2 RNA vaccine is not equally effective against variants of the SARS-CoV2 wildtype virus. In addition, as can be seen from FIG. 2, even where individuals were vaccinated early such as first responders and medical personnel, the protective effect against a new infection began to wane after a relatively short period of time.

In an effort to address this pressing need, numerous candidate anti-SARS-CoV2 vaccine compositions have been developed that target one or more proteins of the virus (see e.g., *FIMMU* 2020, 11:602256). For example, Sinovac and Sinopharm are currently testing inactivated virus vaccine preparations. Cansino Biologics, Janssen Pharma, Oxford University, and Garnaleya have developed vaccines based on a non-replicating adenoviral vector that encodes one or more viral proteins. Novamax produced a protein subunit-based vaccine. More recently, RNA-based vaccines from Moderna and Pfizer have been approved in several jurisdictions. Most of these vaccines induce at least some (typically non-sterile) immunity against infection leading to disease, but it is unclear whether protection is effective across different variants or even strains, whether protection is effective over several months, and/or if sufficient immune memory protects an inoculated individual over extended periods. In addition, it is unclear whether such vaccines generate clinically meaningful T cell-based responses. Unfortunately, and despite the relatively large number of vaccine formulations in development and use, none of the known vaccine compositions were shown to be cross-reactive against other coronaviruses such as MERS-CoV, OC43-CoV, or HKU1-CoV, thereby limiting the usefulness of such vaccines, and to elicit a durable memory B and T cell population.

Thus, even though various vaccine compositions and methods targeting coronaviruses are known in the art, all or almost all of them suffer from several drawbacks, particularly where the vaccine is highly specific against only a single variant of a specific strain. Therefore, there remains a need for improved coronavirus compositions and methods that are effective against a variety of coronavirus strains and variants thereof.

SUMMARY OF THE INVENTION

The inventive subject matter is directed to various vaccine compositions and methods of generating an immune response against multiple coronaviruses, including SARS-CoV1, SARS-CoV2, MERS-CoV, OC43-CoV, and HKU1-CoV. Remarkably, the vaccine compositions presented herein targeting both S (spike protein) and N (nucleocapsid) of SARS-CoV2 exhibited unexpected cross-reactivity against a variety of other coronaviruses, and particularly against SARS-CoV1, MERS-CoV, OC43-CoV, and HKU1-CoV in addition to SARS-CoV2. Even more remarkably, the vaccine compositions presented herein also produced cross-reactive memory B cells as well as cross-reactive memory T cells with cross-reactivity spanning a relatively wide range of different coronaviruses.

In one aspect of the inventive subject matter, the inventor contemplates a method of eliciting in a subject a cross-reactive immune response against a coronavirus that includes a step of administering to the subject a recombinant vaccine composition in a prime and/or boost administration. In such method the recombinant vaccine composition has (a) a first portion encoding a severe acute respiratory syndrome (SARS) coronavirus nucleocapsid protein (N) that is fused to an endosomal targeting sequence (N-ETSD), wherein the first portion is functionally coupled to one or more regulatory elements that enable N-ETSD expression, and (b) a second portion encoding a SARS virus spike protein (S), wherein the second portion is functionally coupled to one or more regulatory elements that enable S expression. The vaccine composition is administered to the subject in an amount that elicits the cross-reactive immune response, wherein the cross-reactive immune response extends from SARS-CoV2 to a serologically distinct variant of SARS-CoV2, and/or to a coronavirus other than SARS-CoV2. Most typically, the coronavirus other than SARS-CoV2 is SARS-CoV1, MERS-CoV, OC43-CoV, and/or HKU1-CoV.

In some embodiments, the immune response is generation of antibodies that bind to at least two of the serologically distinct variants of SARS-CoV2 and/or to SARS-CoV2 and at least one coronavirus other than SARS-CoV2, and in other embodiments the immune response is generation of cytotoxic T cells that have cytotoxicity against different cells harboring respective serologically distinct variants of SARS-CoV2, and/or cells harboring SARS-CoV2 and cells harboring a coronavirus other than SARS-CoV2. In further embodiments, the immune response is generation of cross-reactive memory T cells, and in yet other embodiments the immune response is generation of cross-reactive memory B cells.

Preferably, the N protein is from SARS-CoV-2, and it is contemplated that the endosomal targeting sequence of the N-ETSD is encoded at a 5'-end of the first portion or at a 3'-end of the first portion. Moreover, it is preferred that the first and second portions are arranged in a bicistronic sequence. For example, the N-ETSD may have an amino acid sequence that has at least 90% identity to amino acid sequence SEQ ID NO:1 or have an amino acid sequence SEQ ID NO:1. In other examples, the first portion may have a nucleotide sequence SEQ ID NO:2.

With regard to the S protein it is contemplated that the S protein may have an amino acid sequence that has at least 90% identity to amino acid sequence SEQ ID NO:3 or SEQ ID NO:4, or that the S protein has amino acid sequence SEQ ID NO:3 or SEQ ID NO:4. For example, the second portion may have the nucleotide sequence SEQ ID NO:5 or the nucleotide sequence SEQ ID NO:6.

In further contemplated aspects, the recombinant vaccine composition may be formulated as a recombinant virus, and most preferably as an adenovirus having an E1 gene region deletion and an E2b gene region deletion. Alternatively, or additionally, the recombinant vaccine composition is formulated as a recombinant RNA, preferably a polycistronic RNA comprising the first and second portions. Where desired, the recombinant vaccine composition may also be formulated as a recombinant DNA that preferably comprises the first and second portions.

It is still further contemplated that the recombinant vaccine composition is administered in the prime and the boost administration. Preferably, but not necessarily, the recombinant vaccine composition is formulated as an adenoviral vaccine composition.

In yet other embodiments, the recombinant vaccine composition is administered only in the boost administration. In such case, the boost administration may follow a prime vaccination using a vaccine such as an RNA vaccine, a DNA vaccine, a viral vaccine, or a subunit vaccine. Exemplary RNA vaccine prime vaccination may be self-amplifying self-adjuvant RNA vaccines (that preferably comprise an RNA encoding a coronavirus S protein and/or a coronavirus N protein), and exemplary viral vaccine prime vaccination may comprise an adenoviral viral vaccine (that preferably comprises a recombinant nucleic acid encoding only a coronavirus S protein).

In another aspect of the inventive subject matter, the inventor contemplates a method of generating memory B cells and/or memory T cells having cross-reactivity against multiple distinct coronaviruses where the method includes a step of administering to a subject a recombinant vaccine composition in a prime and/or boost administration, wherein the recombinant vaccine composition has (a) a first portion encoding a severe acute respiratory syndrome (SARS) coronavirus nucleocapsid protein (N) that is fused to an endosomal targeting sequence (N-ETSD), wherein the first portion is functionally coupled to one or more regulatory elements that enable N-ETSD expression, and (b) a second portion encoding a SARS virus spike protein (S), wherein the second portion is functionally coupled to one or more regulatory elements that enable S expression. It is contemplated that the memory B cells produce antibodies that are cross reactive. Most typically, the vaccine composition is administered in an amount that elicits formation of the cross-reactive memory B cells and/or memory T cells. Most typically, the multiple distinct coronaviruses include SARS-CoV1, SARS-CoV2, MERS-CoV, OC43-CoV, and HKU1-CoV.

It is further generally preferred that the nucleocapsid protein N is from SARS-CoV-2, which may further include an endosomal targeting sequence at the 5'-end or the 3'-end. In further preferred aspects, the first and second portions are arranged in a bicistronic sequence. For example, the N-ETSD may have an amino acid sequence that has at least 90% identity to amino acid sequence SEQ ID NO:1, or have the amino acid sequence SEQ ID NO:1. Therefore, the first portion has nucleotide sequence SEQ ID NO:2.

The spike S protein preferably an amino acid sequence that has at least 90% identity to amino acid sequence SEQ ID NO:3 or SEQ ID NO:4, or has the amino acid sequence SEQ ID NO:3 or SEQ ID NO:4. Therefore, the second portion may have the nucleotide sequence SEQ ID NO:5 or SEQ ID NO:6.

As will be readily appreciated, the recombinant vaccine composition may be formulated as a recombinant virus (e.g., adenovirus having an E1 gene region deletion and an E2b gene region deletion) or may be formulated as a recombinant RNA (e.g., polycistronic RNA comprising the first and second portions), or may be formulated as a recombinant DNA (e.g., comprising the first and second portions).

Viewed from a different perspective, the inventor also contemplates a kit that includes a first recombinant vaccine composition that has (a) a first portion encoding a severe acute respiratory syndrome (SARS) coronavirus nucleocapsid protein (N) that is fused to an endosomal targeting sequence (N-ETSD), wherein the first portion is functionally coupled to one or more regulatory elements that enable N-ETSD expression, and (b) a second portion encoding a SARS virus spike protein (S), wherein the second portion is functionally coupled to one or more regulatory elements that enable S expression. The kit will also include a second recombinant vaccine composition that has (a) a recombinant viral vaccine comprising a recombinant nucleic acid encoding a SARS virus spike protein (S), functionally coupled to one or more regulatory elements that enable S expression; or (b) a self-amplifying self-adjuvant RNA vaccine comprising a recombinant nucleic acid encoding a SARS virus spike protein (S), functionally coupled to one or more regulatory elements that enable S expression, and optionally further encoding a severe acute respiratory syndrome (SARS) coronavirus nucleocapsid protein (N) functionally coupled to one or more regulatory elements that enable N expression; or (c)

a subunit vaccine comprising a recombinant protein of a corona virus; or (d) a heat inactivated coronavirus vaccine composition.

Therefore, the inventors contemplate a recombinant vaccine composition for use as a vaccine that elicits in a subject a cross-reactive immune response against a coronavirus, characterized in that the recombinant vaccine composition has (a) a first portion encoding a severe acute respiratory syndrome (SARS) coronavirus nucleocapsid protein (N) that is fused to an endosomal targeting sequence (N-ETSD), wherein the first portion is functionally coupled to one or more regulatory elements that enable N-ETSD expression, and (b) a second portion encoding a SARS virus spike protein (S), wherein the second portion is functionally coupled to one or more regulatory elements that enable S expression. Preferably, the cross-reactive immune response extends from SARS-CoV2 to a serologically distinct variant of SARS-CoV2, and/or from SARS-CoV2 to a coronavirus other than SARS-CoV2.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 4A depicts cross-reactivity results for MERS-CoV, FIG. 4B depicts cross-reactivity results for HCoV-HKU1, FIG. 4C depicts cross-reactivity results for HCoV-OC43, and FIG. 4D depicts a time course for cross-reactivity.

DETAILED DESCRIPTION

The inventor has now discovered that various SARS-CoV2 vaccine compositions that included a nucleocapsid component unexpectedly elicited cross-reactive immune responses in human and non-human subjects upon administration, and particularly as boost administration. Notably, the cross-reactivity extended not only across different SARS-CoV2 strains but also to other members of the coronaviridae family, including SARS-CoV1, MERS-CoV, OC43-CoV, and/or HKU1-CoV. Even more notably, the cross reactivity was a durable response in which cross-reactive memory T cells and memory B cells were observed as is described in more detail below.

Figure 1:
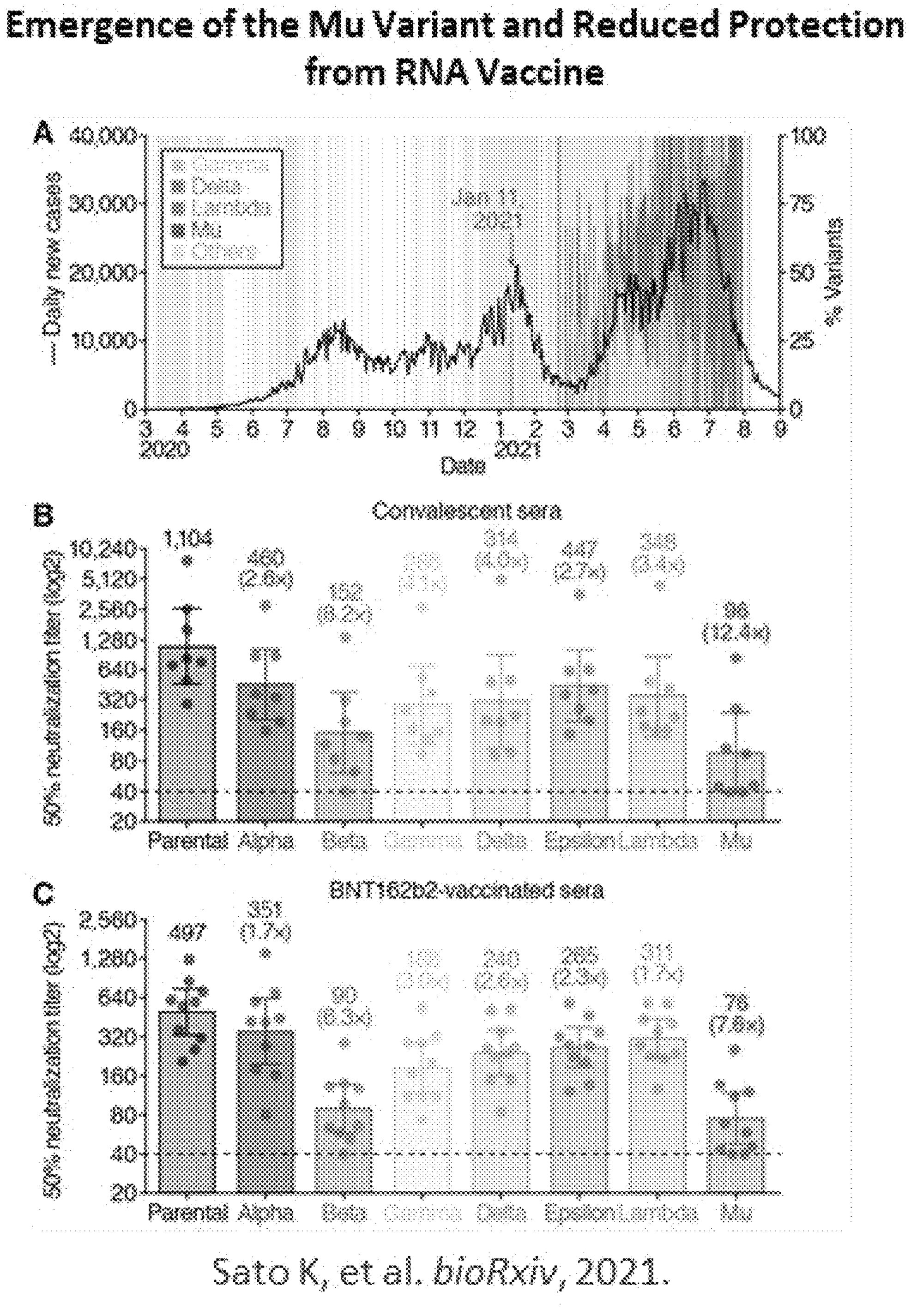
FIG. 1 is a schematic illustration depicting differences in efficacy of a SARS-CoV2 RNA vaccine against various strains of SARS-CoV2.
Figure 2:
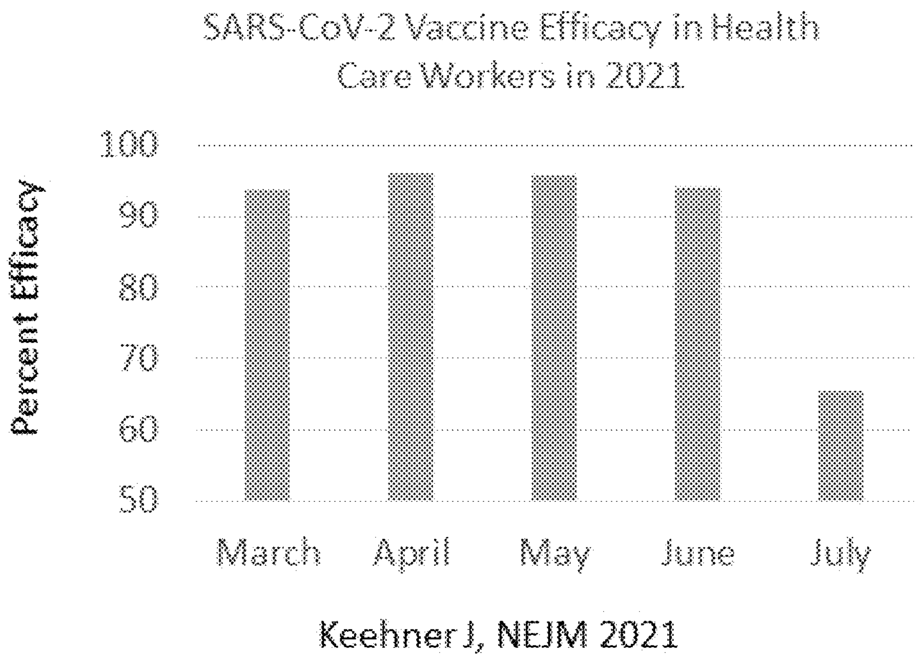
FIG. 2 is a schematic illustration depicting decline in protective effect of a SARS-CoV2 RNA vaccine.
Figure 3:
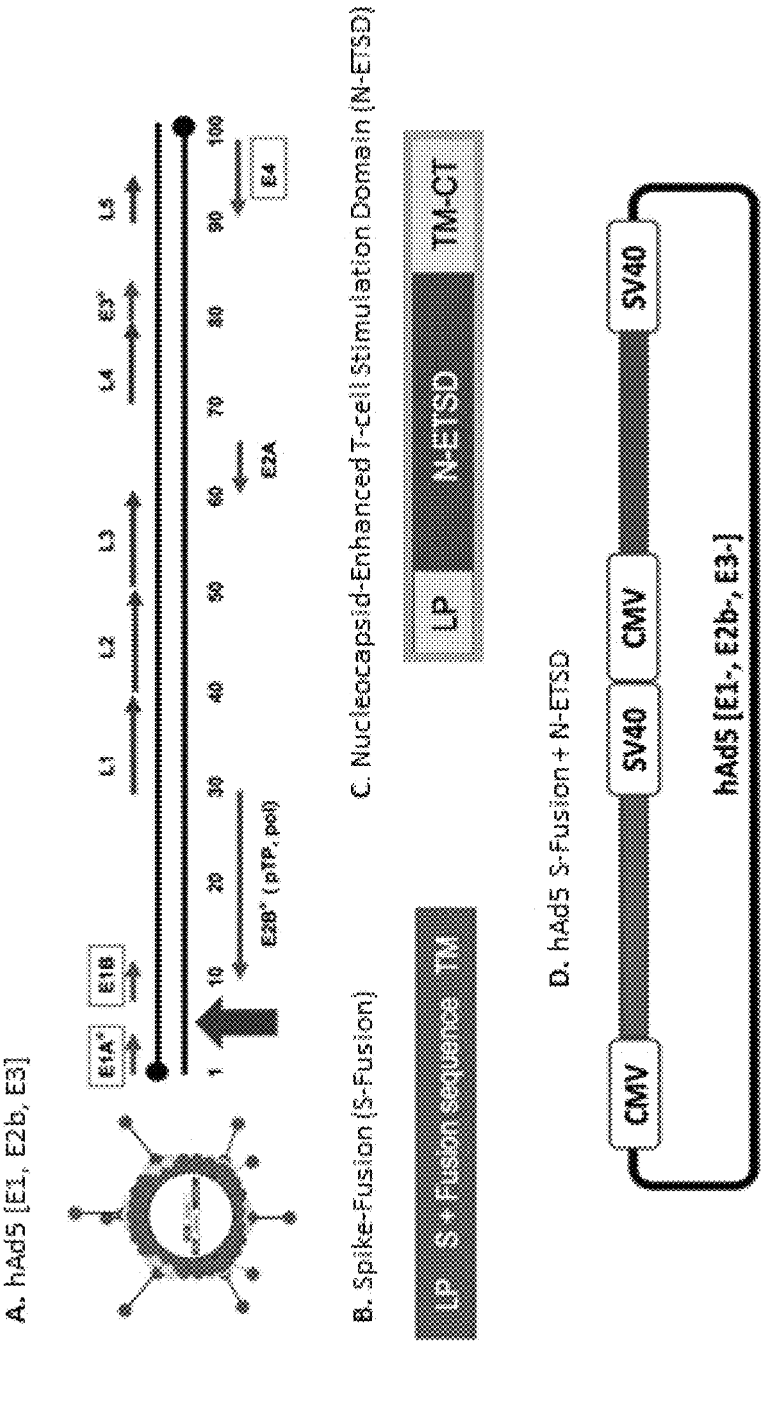
FIG. 3 depicts a schematic of an exemplary recombinant hAd5 virus used for cross-reactive vaccine compositions and methods presented herein.

For example, one vaccine composition that included both a S component and an N component is shown in FIG. 3 in which the vaccine composition is formulated as a recombinant human adenovirus, and especially hAd5 with deletions in E1, E2b, and E3. Inserted into the viral genome is a recombinant nucleic acid that has a first segment that encodes an S-Fusion protein (comprising the S protein of SARS-CoV2 fused to a segment that enhances expression of the fusion protein) and a second segment that encodes N-ETSD (comprising the N protein of SARS-CoV2 and an endosomal targeting segment). As can be taken from FIG. 3, both S-Fusion and N-ETSD are under the control of a strong constitutive CMV promotor to so drive expression of the recombinant SARS-CoV2 proteins in a cell infected with the recombinant virus.

The above adenovirus-based vaccine comprising the hAd5 S-Fusion+N-ETSD used the unique and only clinically available human Adenovirus (hAd5) vector technology without adenoviral fiber production due to the deletions of the E1, E2b, E3 genes and allowed for a potent, long-lasting protein production for maximal cellular and humoral immunity. Moreover, such recombinant adenovirus had shown a proven safety profile in 13 Phase I/II clinical trials in over 125 elderly and immuno-compromised cancer patients. In addition, the recombinant adenovirus of FIG. 3 generated antigen specific CD4+ and CD8+ T cell in patients, even with previous adenoviral immunity. Thus, it should be appreciated that the recombinant adenovirus technology afforded a unique vaccine construct that maximized cell mediated immunogenicity and reduced the risk of antibody dependent enhancement. Still further, it should be recognized that such recombinant viruses can be prepared in high quantities using an established cell line, and that such vaccines are stable at simple refrigeration (2-8° C.).

While the recombinant viral vaccine construct is generally preferred in contemplated uses and methods, it should be recognized that numerous modifications can be performed lo long as the vaccine construct includes a N-protein component. Consequently, it should be appreciated that the recombinant constructs include recombinant viruses and recombinant yeasts, each of which contain a recombinant nucleic acid that will lead to expression of the N-protein (or modification and/or portion thereof) and S-protein (or modification and/or portion thereof).

In one embodiment, the N-ETSD polypeptide may comprises a sequence with at least 80% identity to SEQ ID NO:1. In other embodiments, the identity value is at least 85%. In still other embodiments, the identity value is at least 90%. In some embodiments, the identity value is at least 95%. In some embodiments, the identity value is at least 99%. In some embodiments, the identity value is 100%. It is further contemplated that the N-ETSD fusion protein contains a linker between the N-ETSD domain and the nucleocapsid protein. For example, this linker may be a 16 amino acid linker having the sequence $(G_3S)_4$. In certain embodiments, methods are disclosed herein for enhancing the immunogenicity of an intracellular antigen, the methods comprising tagging the antigen with ETSD and expressing the tagged antigen in an antigen-presenting cell (e.g., a dendritic cell).

In some embodiments, the fusion protein comprising N-ETSD and CoV-2 nucleocapsid protein may be encoded by a nucleic acid sequence having at least 80% identity to SEQ ID NO:2. In some embodiments, the identity value is at least 85%. In some embodiments, the identity value is at least 90%. In some embodiments, the identity value is at least 95%. In some embodiments, the identity value is at least 99%. In some embodiments, the identity value is 100%.

The CoV-2 spike protein is contemplated to have at least 85% identity to SEQ ID NO:3. In some embodiments, the identity value is at least 85%. In some embodiments, the identity value is at least 90%. In some embodiments, the identity value is at least 95%. In some embodiments, the identity value is at least 99%. In some embodiments, the identity value is 100%. The nucleic acid encoding the CoV-2 spike protein has at least 85% identity to SEQ ID NO:5. In some embodiments, the identity value is at least 85%. In some embodiments, the identity value is at least 90%. In some embodiments, the identity value is at least 95%. In some embodiments, the identity value is at least 99%. In some embodiments, the identity value is 100%.

The CoV-2 spike fusion protein is contemplated to have at least 85% identity to SEQ ID NO:4. In some embodiments, the identity value is at least 85%. In some embodiments, the identity value is at least 90%. In some embodiments, the identity value is at least 95%. In some embodiments, the identity value is at least 99%. In some embodiments, the identity value is 100%. The nucleic acid encoding the CoV-2 spike fusion protein has at least 85% identity to SEQ ID NO:6. In some embodiments, the identity value is at least 85%. In some embodiments, the identity value is at least 90%. In some embodiments, the identity value is at least 95%. In some embodiments, the identity value is at least 99%. In some embodiments, the identity value is 100%.

In a second aspect of this disclosure, provided herein is a recombinant yeast comprising a nucleic acid encoding a protein selected from the group consisting of a coronavirus 2 (CoV-2) nucleocapsid protein, a CoV2 N-ETSD protein, a CoV2 spike protein, a CoV2 spike-fusion protein, and a combination thereof. Moreover, each of these encoded proteins may be further modified as described in more detail below. Preferably, the recombinant yeast is *Saccharomyces cerevisiae.*

In some embodiments of this second aspect, the CoV-2 nucleocapsid protein or variant thereof comprises a sequence with at least 80% identity to SEQ ID NO:1 or SEQ ID NO:7. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

In some embodiment of this second aspect, the CoV-2 spike protein or spike fusion protein comprises a sequence with at least 80% identity to SEQ ID NO:3 or SEQ ID NO:4. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

In some embodiments, the nucleic acid encoding the CoV-2 spike protein or spike fusion protein comprises a sequence with at least 80% identity to SEQ ID NO:5 or SEQ ID NO:6. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

Most preferably, the recombinant virus is administered via subcutaneous or subdermal injection. However, in other contemplated aspects, administration may also be intravenous injection or intramuscular injection. In another aspect, the recombinant virus may be administered intranasally, for example via an intranasal spray. Alternatively, or additionally, antigen presenting cells may be isolated or grown from cells of the patient, infected in vitro, and then transfused to the patient.

In one aspect of any of the embodiments described above or elsewhere herein, the composition is formulated in a pharmaceutically acceptable excipient suitable for administration to a subject.

The immunotherapeutic compositions disclosed herein may be either "prophylactic" or "therapeutic". When provided prophylactically, the compositions of the present disclosure are provided in advance of the development of, or the detection of the development of, a coronavirus disease, with the goal of preventing, inhibiting or delaying the development of the coronavirus disease; and/or generally preventing or inhibiting progression of the coronavirus disease in an individual. Therefore, prophylactic compositions can be administered to individuals that appear to be coronavirus disease free (healthy, or normal, individuals), or to individuals who has not yet been detected of coronavirus. Individuals who are at high risk for developing a coronavirus disease, may be treated prophylactically with a composition of the instant disclosure.

When provided therapeutically, the immunotherapy compositions are provided to an individual who is diagnosed with a coronavirus disease, with the goal of ameliorating or curing the coronavirus disease; increasing survival of the individual; preventing, inhibiting, reversing or delaying development of coronavirus disease in the individual.

In yet another embodiment, disclosed herein is a vaccine composition comprising the adenovirus or yeast as disclosed above, and wherein the composition is formulated for injection. The vaccine composition may be used for inducing immunity against CoV-2 in a patient in need thereof, by administering to the patient the vaccine composition.

Also disclosed herein are methods for preventing and/or treating coronavirus diseases, and especially COVID-19. Preferably, the method includes using a viral or yeast vector that encodes the wild-type or modified form of a nucleocapsid protein and/or the wild-type or modified form of a spike protein of the coronavirus in an immunogenic composition that is administered to a subject individual. The virus and/or yeast vaccine, thus administered, would infect the individual with CoV-2 the wild-type or modified form of the nucleocapsid or spike protein. With that in place, the individual would have an immune response against it, and be vaccinated. Notably, as the nucleocapsid protein and the spike protein are relatively conserved polypeptides, immune responses can be elicited for a variety of members of the coronavirus family.

Where the recombinant vector is an adenovirus, the adenoviral vector may be modified to encode the wild-type or modified form of the nucleocapsid protein, and/or spike protein. Similarly, in case of yeast, the yeast vector may also be modified to encode the wild-type or modified form of the nucleocapsid protein, and/or the spike protein. As is shown in more detail below, positive immune responses were obtained on cell mediated immunity upon administration of immunogenic compositions comprising the viral and/or yeast vectors in patients in need thereof. Thus, in one embodiment, the present disclosure contemplates creating the coronaviral spikes to be expressed on the yeast surface. In such embodiment, the yeast is acting as an avatar coronavirus to stimulate B cells, which then results in humoral immunity.

As disclosed herein is a next generation bivalent human adenovirus serotype 5 (hAd5) vaccine capable of inducing immunity in patients with pre-existing adenovirus immunity, comprising both an S sequence optimized for cell surface expression (S-Fusion) and a conserved nucleocapsid (N) antigen that is designed to be transported to the endosomal subcellular compartment, with the potential to generate durable immune protection. As further described herein, such bivalent vaccine has been found to be optimized for immunogenicity as evidenced by the following findings:

1) The optimized S-Fusion displayed improved S receptor binding domain (RBD) cell surface expression compared to S-WT where little surface expression was detected;
2) The expressed RBD from S-Fusion retained conformational integrity and recognition by ACE2-Fc;
3) The viral N protein modified with an enhanced T-cell stimulation domain (ETSD) localized to endosomal/lysosomal subcellular compartments for MHC I/II presentation; and
4) These optimizations to S and N (S-Fusion and N-ETSD) generated enhanced de novo antigen-specific B cell and CD4+ and CD8+ T-cell responses in antigen-naive pre-clinical models.

Both the T-cell and antibody immune responses to S and N components demonstrated a T-helper 1 (Th1) bias. The antibody responses were neutralizing as demonstrated by independent SARS-CoV-2 neutralization assays. Thus, in one embodiment, the next generation bivalent hAd5 S-Fusion+N-ETSD vaccine provides robust, durable cell-mediated and humoral immunity against SARS-CoV-2 infection. Moreover, and as also further described in more detail below, the vaccine construct may be administered orally, intranasally, or sublingually. Thus, in one embodiment, the instant disclosure also provides beyond injectable formulations (e.g., SC or IM) vaccine constructs in oral, intranasal, and sublingual formulation to induce mucosal immunity in addition to cell-mediated and humoral immunity. Viewed from another perspective, substantial immunity can be generated by injection, oral/mucosal administration, alone or in combination. In one embodiment, the COVID-19 vaccine disclosed herein generates long-term T and B cell memory. Further aspects, advantages and considerations suitable for use herein are disclosed in our copending International application publication with the publication number WO 2021/183665 (PCT/US21/21737), incorporated by reference herein in its entirety.

Figure 4A:
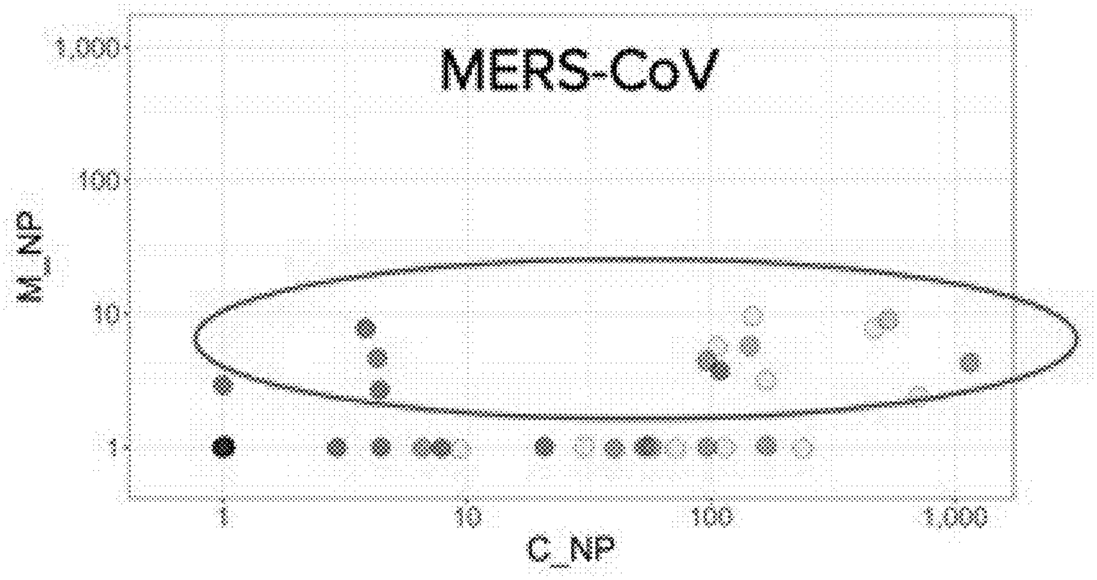
FIGS. 4A-4D depict exemplary results for antibody cross-reactivity in individuals after vaccination with the recombinant hAd5 virus of FIG. 3.
Figure 4B:
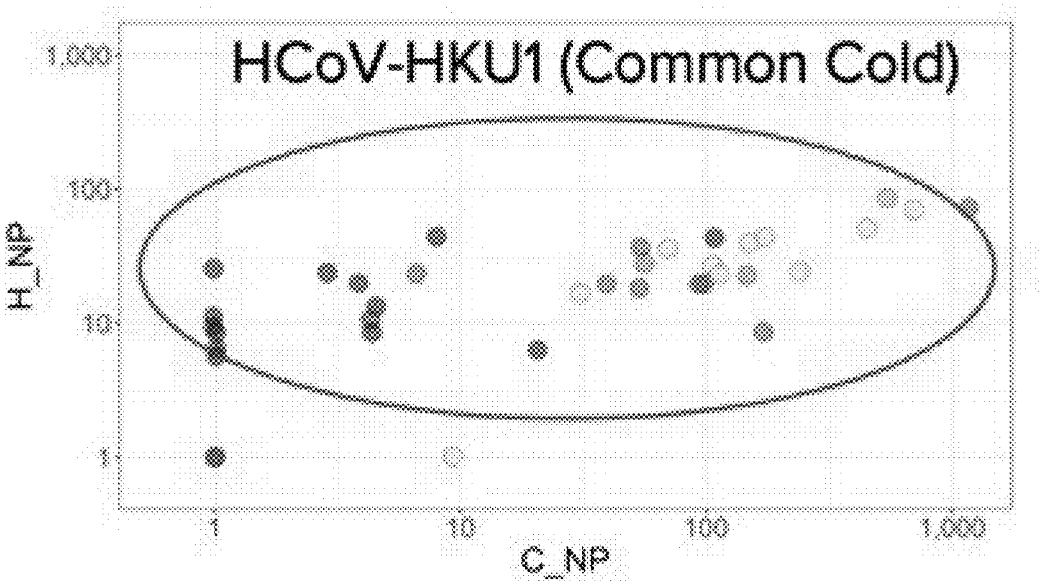
Figure 4C:
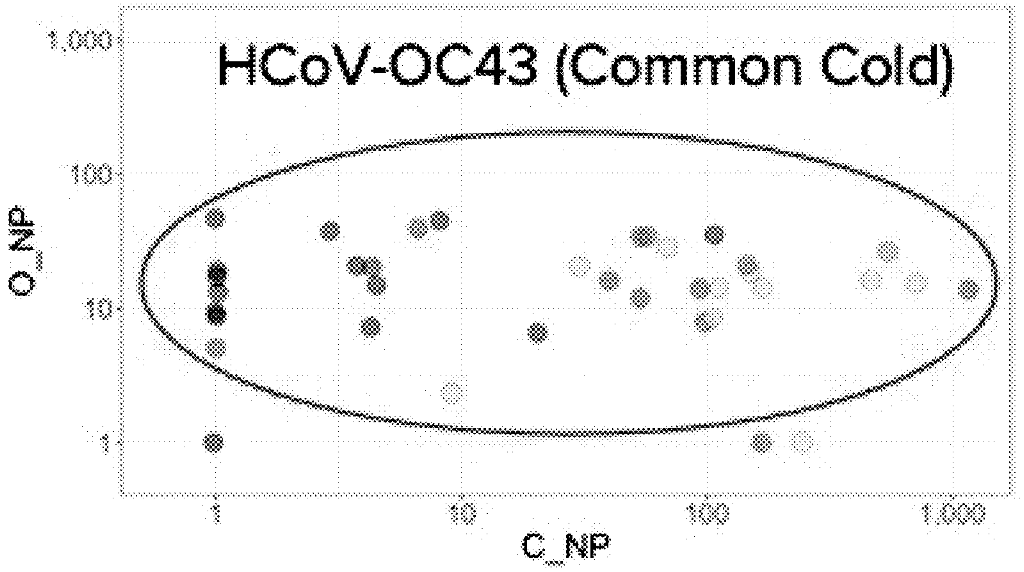
Figure 4D:
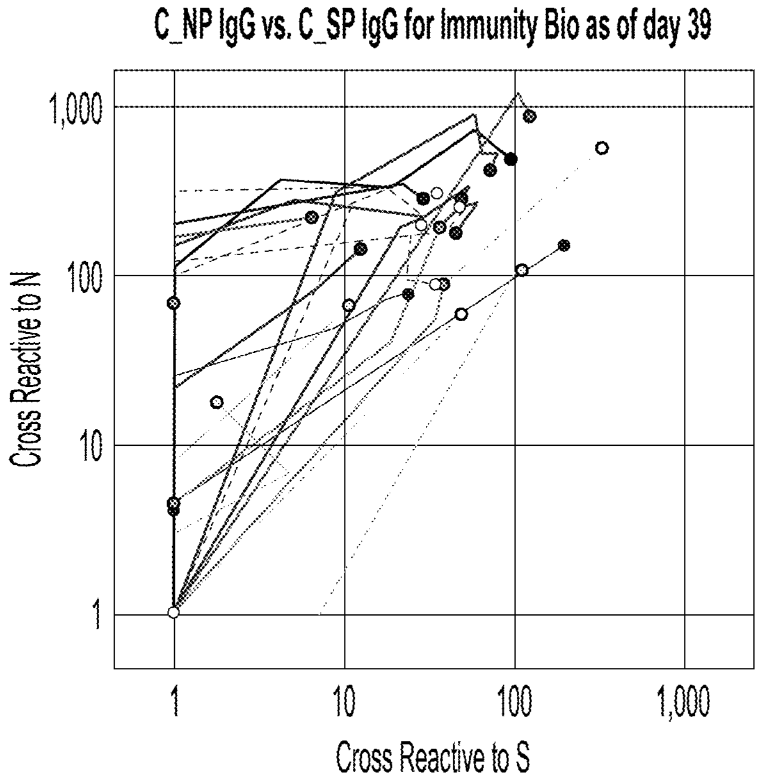

Using the above adenoviral hAd5 S+N vaccine composition as schematically shown in FIG. 3 in a prime and boost regimen in human (healthy volunteers), the inventor discovered that the vaccine composition after boost elicited not only a robust immune response against S and N of SARS-CoV2, but that the antibodies of the vaccinated human also had significant cross-reactivity against other coronaviruses, and especially against MERS-CoV, HcoV-HKU1, and HCoV-OC43 as is exemplarily shown in FIG. 4A, FIG. 4B, and FIG. 4C, respectively. When observing the time course of antibody generation in the vaccinated volunteers, it was observed that the anti-N antibodies rapidly increased relative to anti-S antibodies as can be seen in FIG. 4D. Such finding was entirely unexpected, is attributed to the presence of N as a component in the vaccine, and possibly also attributable to the ETSD sequence that was coupled to the N-protein, directing the N protein to the endosomal presentation pathway via MHC-II and thereby triggering a robust CD4+ response.

Figure 5:
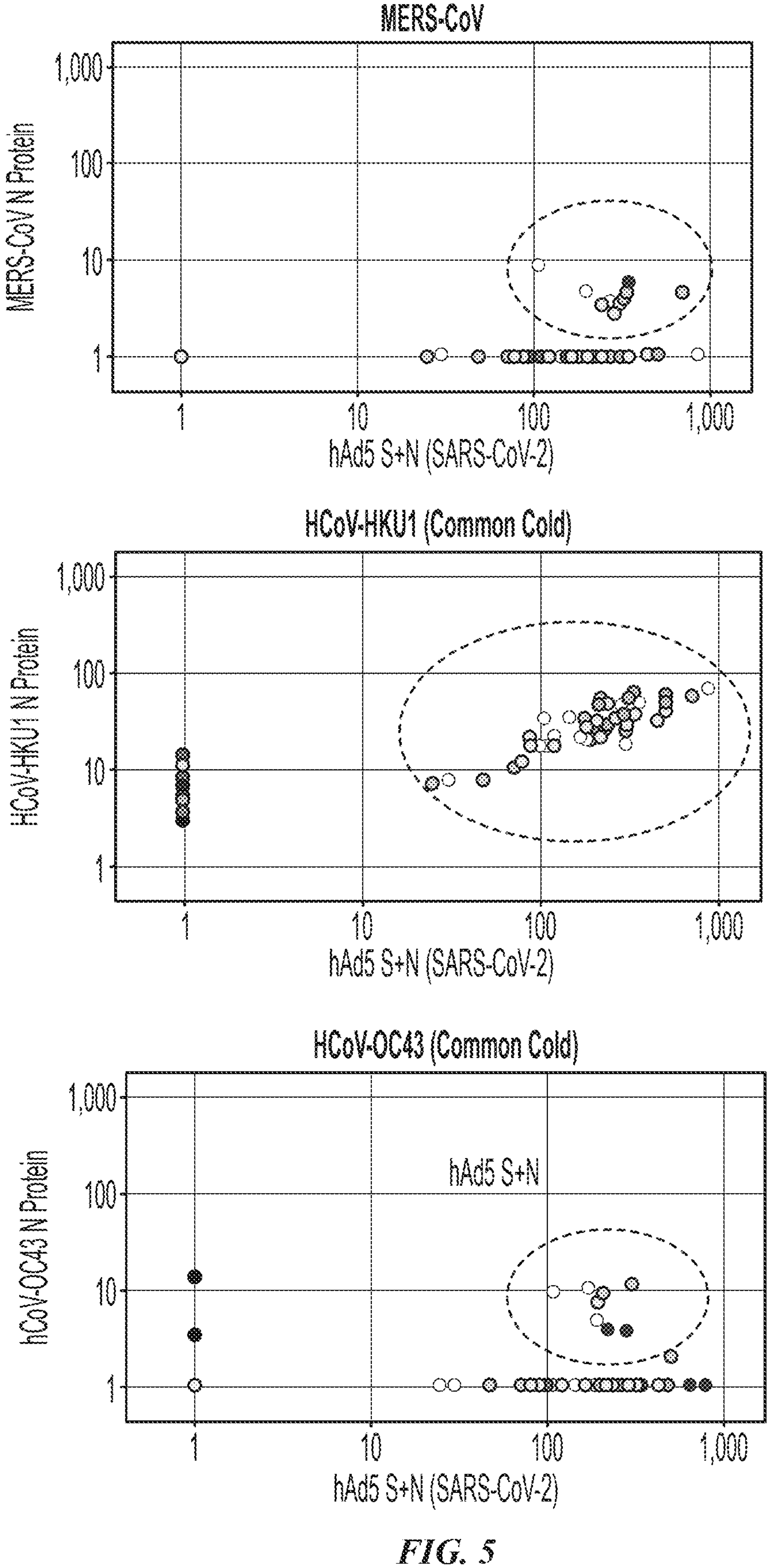
FIG. 5 depicts exemplary results for memory B cells generated in non-human primates after vaccination with the recombinant hAd5 virus of FIG. 3 showing that hAd5 S+N induces cross reactive memory B Cells to N of SARS-CoV-2.
Figure 6:
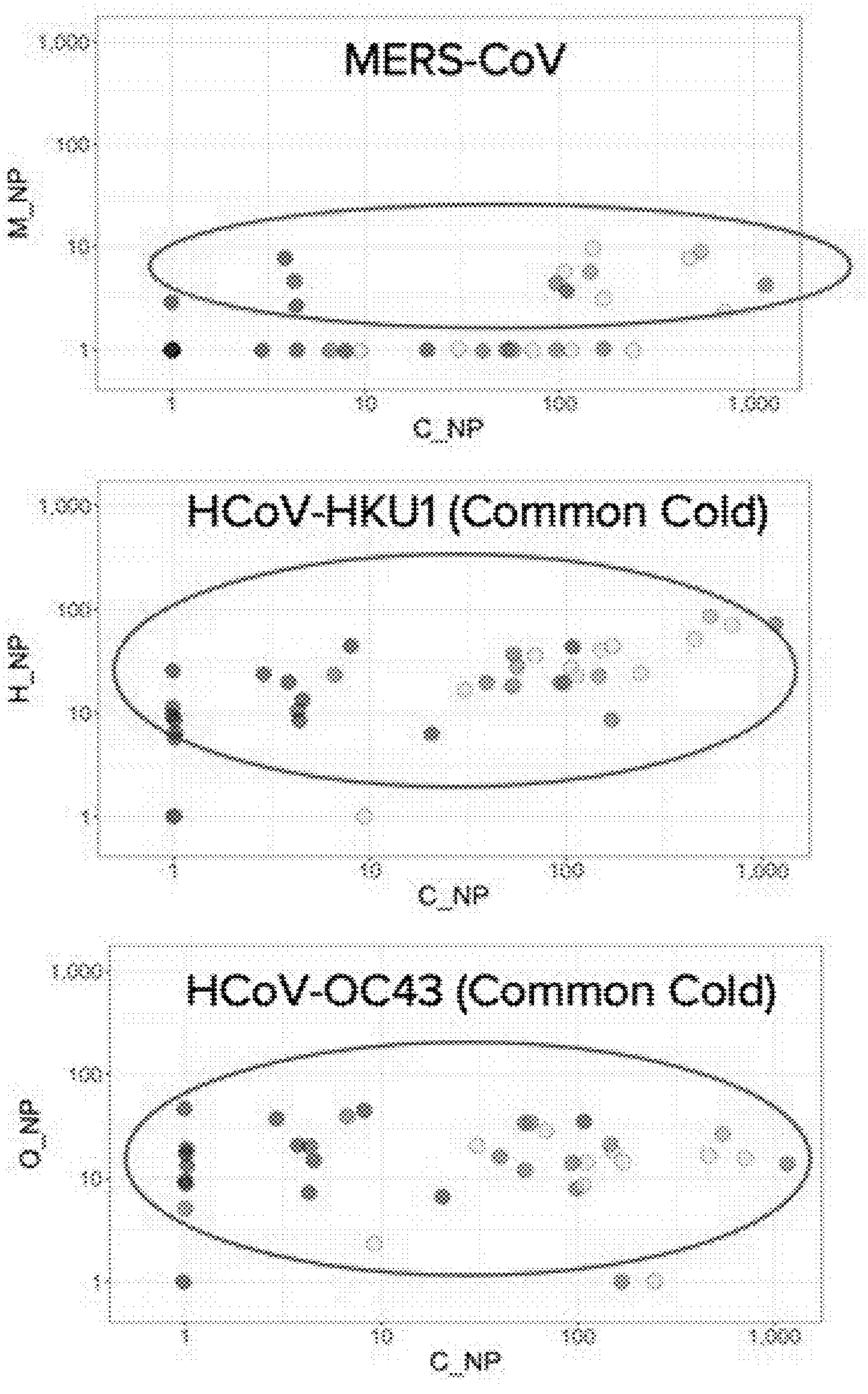
FIG. 6 depicts exemplary results for memory B cells generated in healthy human subjects after vaccination with the recombinant hAd5 virus of FIG. 3 showing that hAd5 S+N induces cross reactive memory B Cells to N of SARS-CoV-2.

Following up on these results, the inventor then sought to identify whether or not the vaccine compositions presented herein would also elicit cross-reactive memory B cells to N in response to the vaccination. Remarkably, the hAd5 S+N vaccine once more elicited generation of cross-reactive memory B cells as is show in the exemplary data of FIG. 5. Here, cross-reactivity was observed against MERS-CoV, HcoV-HKU1, and HCoV-OC43. Similarly, where healthy human volunteers were subjected to prime and boost vaccination with the hAd5 S+N vaccine, the vaccine induced formation of memory B cells as is shown in the exemplary data of FIG. 6. Here once more, cross-reactivity was observed against MERS-CoV, HcoV-HKU1, and HCoV-OC43.

Figure 7:
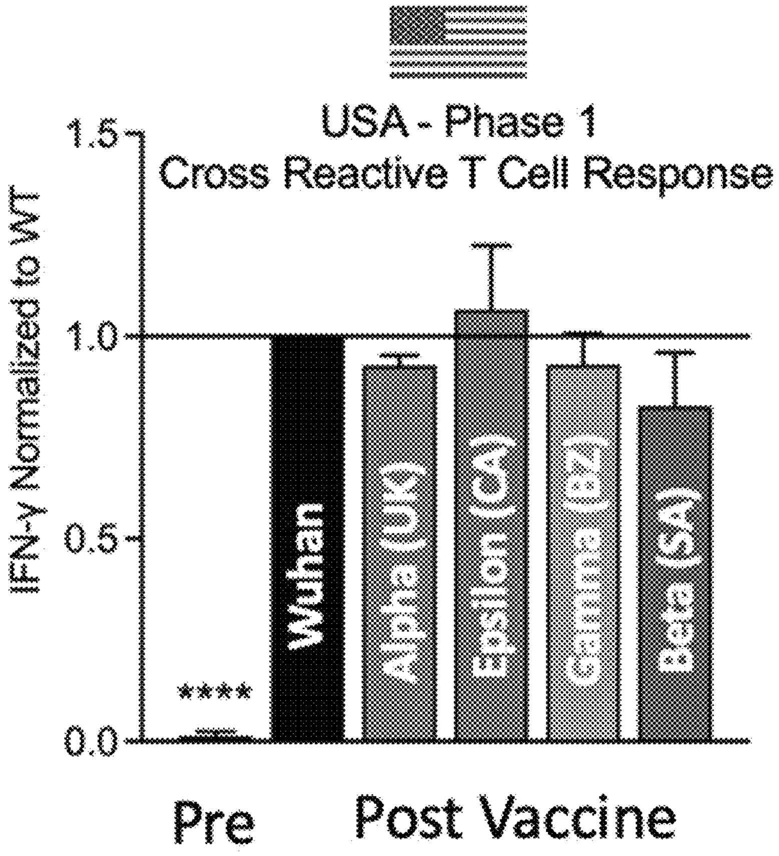
FIG. 7 depicts exemplary results for memory T cells generated in healthy human subjects after vaccination with the recombinant hAd5 virus of FIG. 3 showing that hAd5 S+N induces cross reactive memory B Cells to N of SARS-CoV-2.

A further set of experiments was then conducted to determine whether the hAd5 S+N vaccine would induce formation of cross-reactive memory T cells in healthy human volunteers, and exemplary results are shown in FIG. 7. As is readily apparent, the vaccine was effective not only against the wildtype variant, but also across a wide spectrum of variants.

While the above experimental data were obtained under protocols that used the hAd5 S+N vaccine in both prime and boost administrations, it should be appreciated that the vaccine formulations presented herein are suitable for either prime or boost. However, it is especially contemplated that the vaccine compositions presented herein are particularly beneficial where they are employed in a boost administration following a prime administration that may or may not include an N-component. Therefore, contemplated prime vaccine administrations that can be followed with the vaccine composition presented herein include those targeting the S-protein, a fragment of the S-protein (and especially fragments comprising the RBD of the S protein), and/or fusion proteins of the S-protein or fragment thereof.

Figure 8:
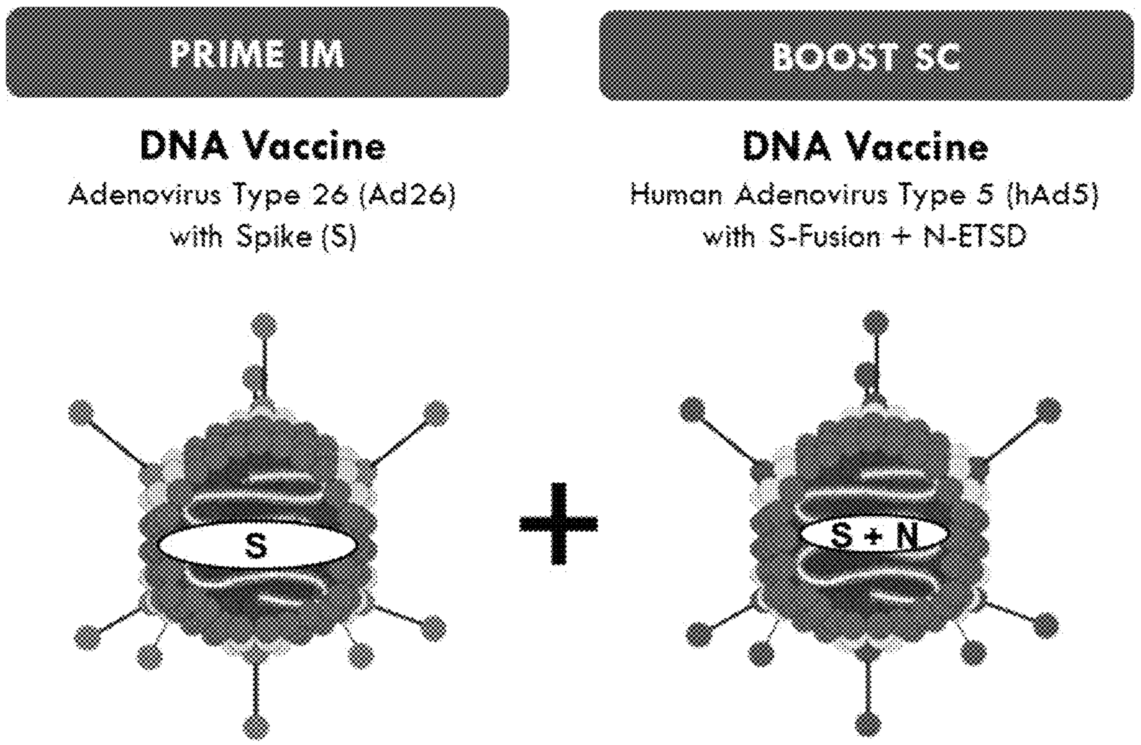
FIG. 8 depicts one exemplary prime-boost vaccine regimen using the recombinant hAd5 virus of FIG. 3.
Figure 9:
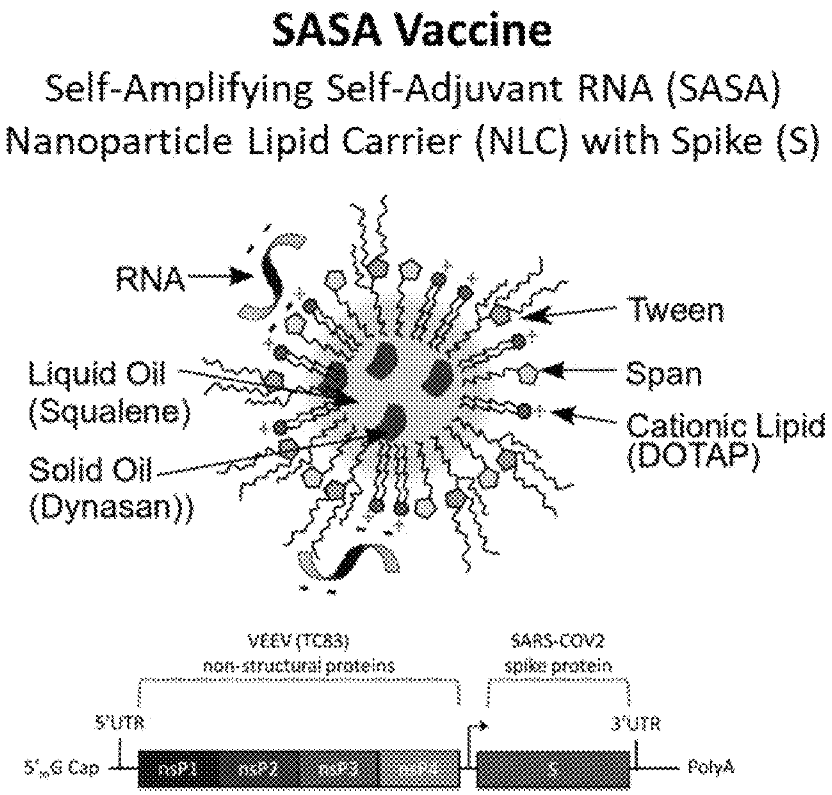
FIG. 9 depicts an exemplary SASA vaccine composition suitable for use in a prime-boost vaccine regimen using the recombinant hAd5 virus of FIG. 3.

For example, a suitable prime/boost regimen is schematically depicted in FIG. 8 where the prime vaccination uses a recombinant adenovirus (here: Ad26) that includes a nucleic acid encoding the S protein. The boost vaccination the uses the hAd5 S+N vaccine as schematically shown in FIG. 3. Alternatively, the prime vaccination need not be based on a recombinant virus as described above but may also employ a SASA-type vaccine composition in which a nucleic acid encoding the S and/or N protein is coupled to a lipid carrier to so form a self-amplifying self-adjuvant RNA or DNA vaccine as exemplarily shown in FIG. 9. SASA-type vaccines have a variety of benefits over nanoparticle-based RNA vaccines (e.g., such as those provided by Pfizer or Moderna). The table below illustrates exemplary benefits for SASA-type vaccines in contrast to nanoparticle-based RNA vaccines.

| Limitation | Current RNA Vaccines | ImmunityBio RNA Vaccines |
|---|---|---|
| Storage/ Distribution | Requirement for deep-cold chain. | NLC formulation allows for storage at room temperature for years |
| Potency | Elicit immunity at levels similar to recovered patients, which may allow re-infection. | Self replicating RNA allows for increased potency, allowing for potential single shot protection |
| Duration of Immunity | Modest immunogenicity may be associated with short durability | Self-Adjuvanting RNA vaccine platform may increase duration and breadth of immunity |
| Protection against mutant SARS-CoV-2 strains | RNA sequence encapsulated within delivery vehicle making adaptations to new strains challenging | RNA decorated on outside of NLC, allowing for easy swapping of genetic sequence. Demonstrated ability to vaccinate with multivalent strains |

Figure 10:
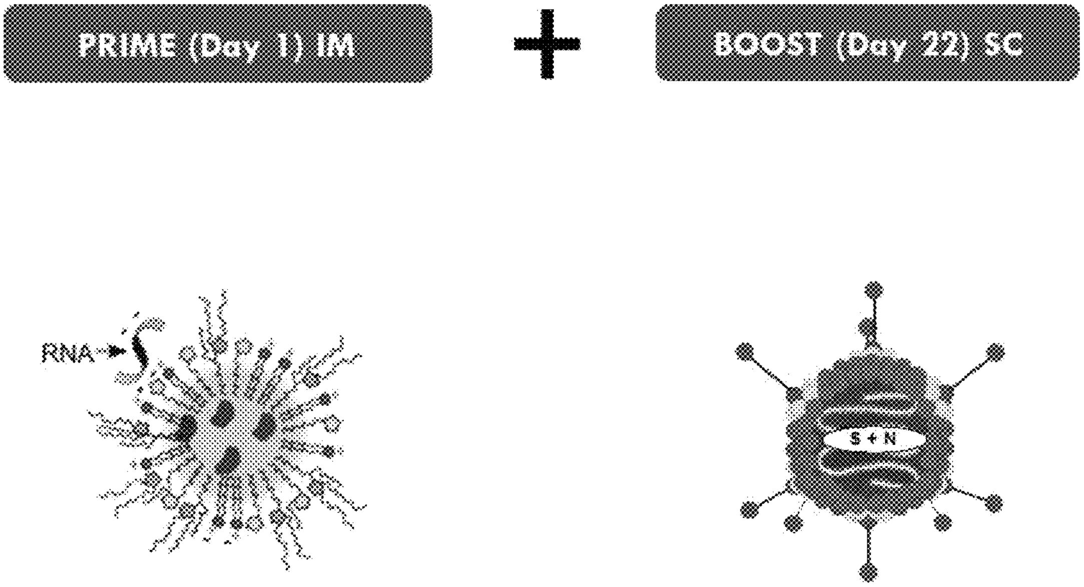
FIG. 10 depicts another exemplary prime-boost vaccine regimen using the recombinant hAd5 virus of FIG. 3.

Therefore, the inventor also contemplates use of a SASA-prime vaccination as exemplarily shown in FIG. 10, followed by a recombinant viral boost vaccination using the hAd5 S+N vaccine as exemplarily shown in FIG. 3. In this context, it should be appreciated that a heterologous prime boost ("Mix and Match") vaccine regimen has been shown to elicit some of the strongest and potentially most durable immune responses to COVID. In particular, a "Prime" vaccine with an RNA vaccine led to strong antibody response, while a "Boost" vaccine with a recombinant adenovirus vaccine makes for strong cellular immune responses. Such vaccine strategy as exemplarily outlined in FIG. 10 is believed to deliver a strong antibody response: Potent Th1 antibodies to both wildtype and beta variant, and a strong immune cell response: Potent CD8+ T cells to both S and N for wildtype and beta variant, and potent CD4+ T cells to both S and N for wildtype and beta variant.

Therefore, it is contemplated that any given prime vaccination against SARS-CoV2 can be substantially augmented with a boost vaccination using the hAd5 S+N vaccine as exemplarily shown in FIG. 3 (or other vaccine formulation that includes an N-component). Indeed, the hAd5 S+N vaccine is also deemed to be suitable where an individual has already received a prime and boost vaccination (e.g., a Pfizer, Moderna, or Johnson & Johnson vaccine). Such additional boost is believed to confer the same advantages with regard to cross-reactivity and memory B and memory T cell formation.

In still further contemplated aspects of the inventive subject matter, and particularly where the recombinant S and/or N protein is expressed in yeast or another suitable expression systems, the recombinant protein(s) can be combined as subunit vaccines with adjuvant 3M-052-Alum (which was developed by IDRI and 3M). As was unexpectedly observed, the 3M-052-Alum adjuvant also elicited significant cross-reactivity against other SARS-CoV variants and even other coronaviruses. Therefore, the N/N-ETSD and S/S-Fusion sequences presented herein are particularly contemplated for such subunit vaccines having the 3M-052-Alum adjuvant.

Figure 11:
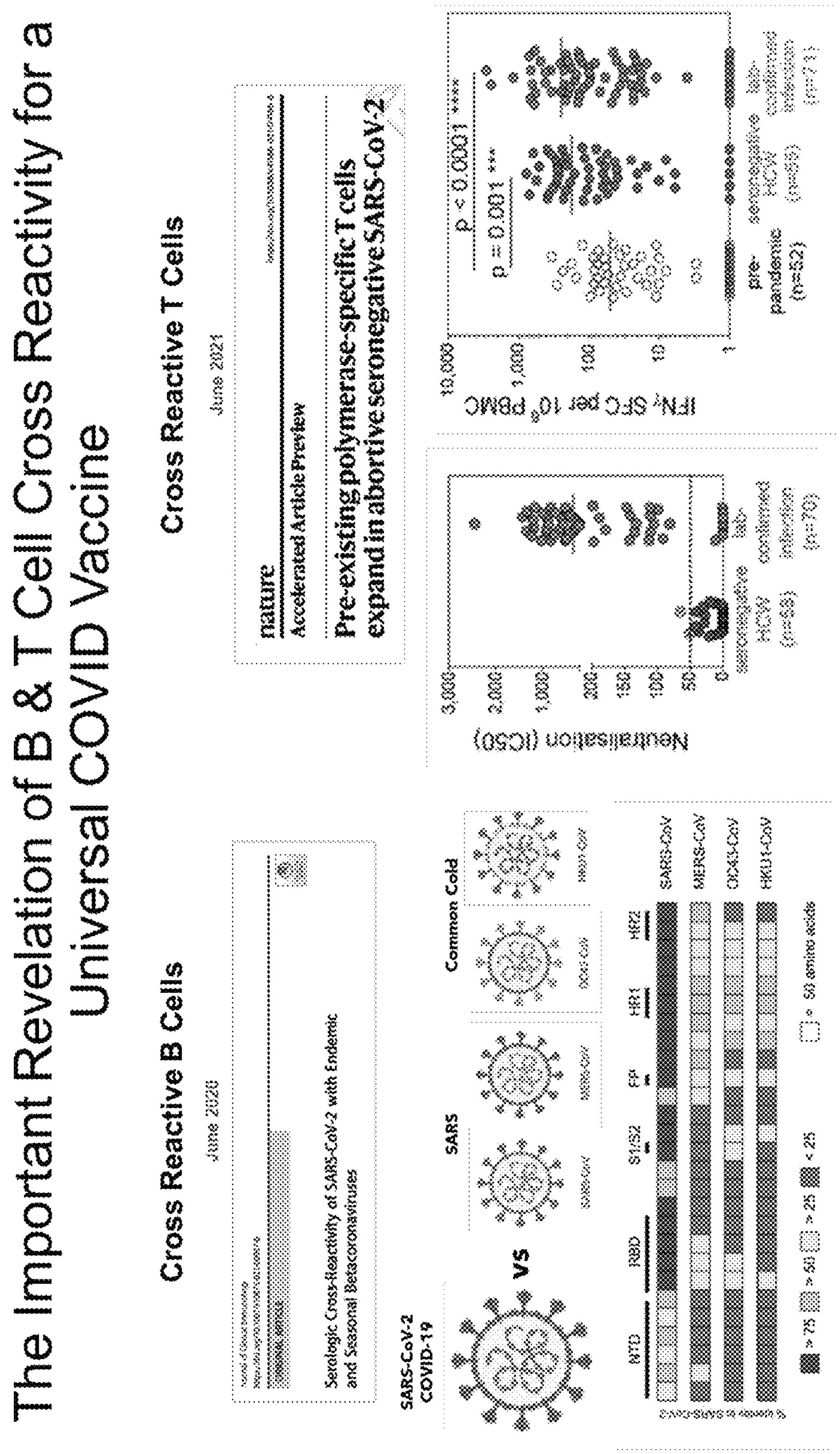
FIG. 11 depicts an exemplary B and T cell cross reactivity for a universal COVID vaccine.

The important revelation of B and T cell cross reactivity for a universal COVID vaccine is illustrated in FIG. 11. Hicks J, et al (Serologic cross-reactivity of SARS-CoV-2 with endemic and seasonal Betacoronaviruses. J Clin Immunol. 2021 Mar. 16, which is incorporated by reference herein) discloses the cross-reactivity potential of SARS-CoV-2 antibodies with the full spike proteins of four other Betacoronaviruses that cause disease in humans, MERS-CoV, SARS-CoV, HCoV-OC43, and HCoV-HKU1. It was found that there was potential cross-reactivity of antibodies against SARS-CoV-2 towards the four other coronaviruses, with the strongest cross-recognition between SARS-CoV-2 and SARS/MERS-CoV antibodies, as expected based on sequence homology of their respective spike proteins.

The results disclosed herein support the inclusion of non-spike antigens in second-generation vaccines. In particular, the T cells induced by common cold coronaviruses play a protective role against SARS-COV2 infection. These T cells provide protection by attacking proteins within the virus, rather than the spike protein on its surface. The spike protein is under intense immune pressure from vaccine-induced antibody which drives evolution of vaccine escape mutants. In contrast the internal proteins targeted by the T cells mutate much less. Consequently, they are highly conserved between the various SARS-CoV-2 variants, including Omicron. Thus, the presently disclosed vaccines, which induce broadly protective T cell responses, provide a better protection against current and future SARS-CoV-2 variants.

Figure 12:
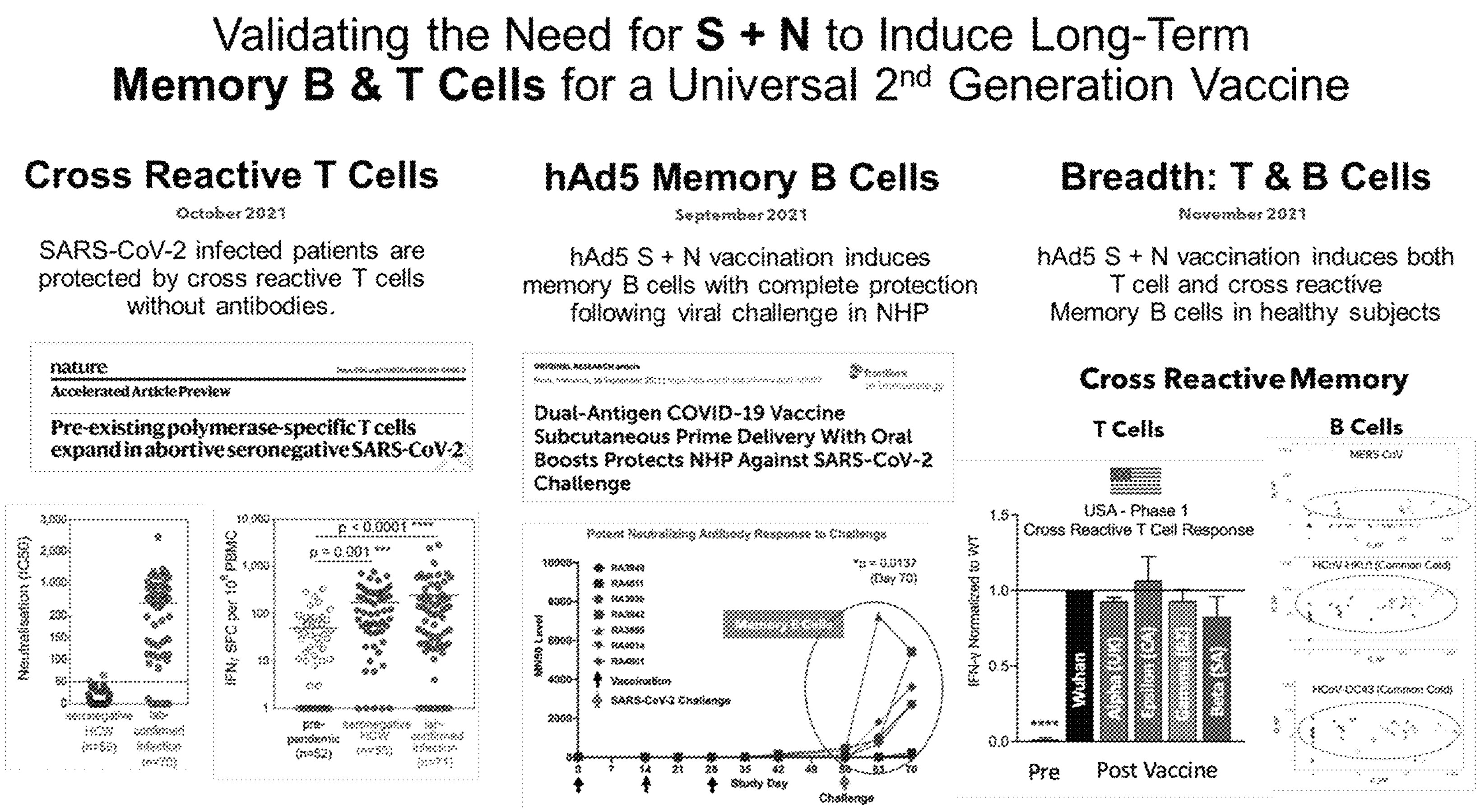
FIG. 12 depicts an exemplary validation of the need for S+N to induce long-term memory B & T cells for a universal 2nd generation vaccine.
Figure 13:
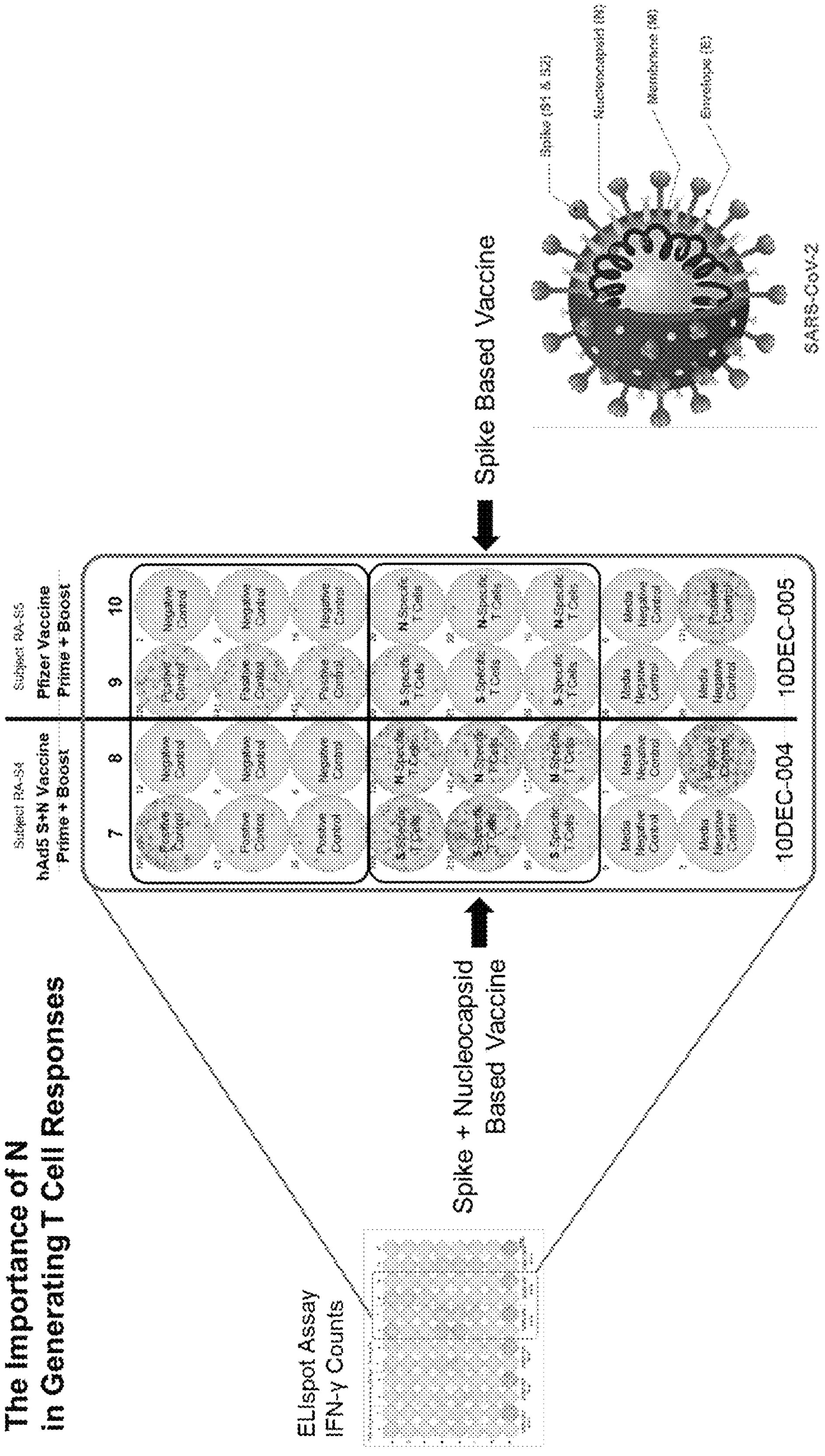
FIG. 13 depicts an exemplary importance of N in generating T cell responses.

FIG. 12 validates the need for both S+N to be present to induce long-term memory B and T cells for a universal 2nd generation vaccine. SARS-CoV-2 infected patients are protected by cross reactive T cells without antibodies. hAd5 S+N vaccination induces memory B cells with complete protection following viral challenge in NHP. hAd5 S+N vaccination induces both T cell and cross-reactive memory B cells in healthy subjects. The importance of N in generating T cell responses is further disclosed in FIG. 13. As can be seen from this figure, the hAd5 S+N Vaccine Prime+Boost schedule as disclosed herein provides better and longer protection as compared to Spike based vaccine. Consequently, the inventors have surprisingly found that the vaccine compositions presented herein targeting both S and N of SARS-CoV2 exhibited unexpected cross-reactivity against a variety of other coronaviruses, and particularly against SARS-CoV1, MERS-CoV, OC43-CoV, and HKU1-CoV in addition to SARS-CoV2.

Embodiments of the present disclosure are further described in the following examples. The examples are merely illustrative and do not in any way limit the scope of the invention as claimed.

Example 1

With respect to the experiments performed and data presented, the following reagents and methods were employed in addition to well-known protocols:

Peptide pools (Pepmix™): 15-mer peptides that overlapped by 11 amino acids and spanned the entire protein sequence of the spike of SARS-CoV-2 (Wuhan, Alpha, Epsilon, Gamma and Beta) were purchased from JPT (JPT Peptide Technologies GmbH, Berlin, Germany).

ELISpot assay: ELISpot plates were coated with human IFNγ and IL-4 antibody (ImmunoSpot, Cleveland, USA) overnight at 4° C. Then, 300,000 PBMCs were seeded per well and stimulated for 44-48 h with SARS-CoV-2 Pepmix™ (2.5 μg/ml/peptide, JPT, Germany), Subsequently, the plates were developed according to kit's instructions (hIFNgIL4-2M/2, Immunospot). Plate were scanned and Spot forming units (SFU) were quantified using ImmunoSpot S6 Universal-V Analyzer with ImmunoSpot MultiSet AutoCount™ software.

Example 2: Cytometric Bead Array Generation

Conjugation of beads with Streptavidin: The Cytometric Bead Array (CBA) used in this analysis was constructed using spherotech 4 um and 5 um carboxy bluepak array kits (cat PAK-4067-8K and PAK-5067-10K respectively). The beads were functionalized by first conjugating Streptavidin (SA) to the beads via commonly employed 1-Ethyl-3-(3-dimethylaminopropyl) carbodiimide (EDC) chemistry. SA (southern biotech cat 7105-01) was buffered exchanged using pd-10 columns (Cytiva 17-0851-01) into PBS and diluted to 2 mg/mL. For conjugation, 10e8 spherotech particles were isolated by centrifugation at 10,000×g for 3 min. After carefully removing the supernatant, the bead pellet was resuspended in 0.5 mLs of SA in PBS. Following complete resuspension by pipetting, 0.5 mLs of 6 mM EDC dissolved in 0.05M MES buffer PH 5.0 was added, and the reaction mixture was rotated at room temperature overnight. After the conjugation reaction was complete, 0.1 mL of 1M tris PH 8.0 was added to quench the reaction. Following a 1 hr incubation rotating at RT, the beads were harvested by centrifugation as described above and washed twice in 1 mL of PBS. Following the final wash, beads were resuspended in 1 mL of PBS with 0.25% NaN3 and stored at 4° C. until use.

SA loading quality assurance: Following SA conjugation, quality control experiments were performed to determine the degree and uniformity (when multiple particle sizes and/or peak identities are used) of labeling by staining the SA-conjugated particles with fluorescently-labeled-biotinylated hemagglutinin (PR8). Individual array constituents were mixed and diluted to 1e6 of each particle/mL. 40 ml of serial dilutions of PR8 were prepared in a 96 well U bottom plates (costar 3797) ranging from 1 ug/mL to 2 ng/mL. 5 ml of the bead suspension was added, mixed by pipetting, and incubated for 15 min at RT. 200 ml of PBS was then added and the plate was centrifuged at 3000×g for 5 min. The beads were resuspended in 80 ml of PBS. Samples were then analyzed by flow cytometry.

Recombinant antigen absorption: Following the SA coupling and quality control procedures described above, biotinylated recombinant array antigens were passively absorbed onto the individual particles. For antigens used in this array configuration, a single biotin site was added enzymatically onto a carboxy terminal AVI tag. SA conjugated particles were harvested by centrifugation as described above and resuspended in 1 mg/mL of the biotinylated recombinant proteins in 1% BSA in PBS. Antigen loading was carried out by rotating overnight at 4° C. Following absorption, the beads were harvested by centrifugation as described, and washed twice with 1% BSA in PBS. Finally, the antigen coated beads were resuspended at 1e8 particles/mL 1% BSA in PBS, 0.25% NaN3 and stored at 4° C. until use.

Ig Standards: To construct indirect standard beads, bead peaks selected for each isotype were combined and biotinylated goat-anti Isotype F(ab)2 Abs (Southern Biotech: anti-IgM 2022-01, anti-IgA 2052-01, and anti-IgG 2042-01) were added at a concentration of 1 mg/mL. Standard bead preparations were washed, harvested, and stored as described for antigen coated beads.

Example 3: Recombinant Antigen Production

Recombinant antigens used in CBA: Recombinant antigens used in this array include influenza H1 Ca09 hemagglutinin (HA) and b-coronavirus (CoV) Spike (SP), Spike subdomains (receptor binding domain (RBD) and N terminal domain (NTD)), and Nucleocapsid protein (N). The recombinant CoV S and N proteins were produced from sequences derived from the 5 known human infectious b-coronaviruses. These include the Wuhan/Washington strain of SARS-CoV-2 (abbreviated C), SARS1 (abbreviated S), MERS (abbreviated M), OC43 (abbreviated O), and HKU1 (abbreviated H). RBD and NTD SP subdomains were produced from sequences derived from Wuhan/Washington strain of SARS-CoV-2. It is contemplated that Influenza Hemagglutinin protein has at least about 80%, at least 85%, at least 90%, at least 95%, at least 99%, or 100% sequence identity to the polypeptide of SEQ ID NO:26.

Production of pre-fusion recombinant Spike (SP) protein: Ectodomain SP pre-fusion trimers (SARS-CoV-2 $S_{14-1211}$) were produced by co-transfecting SP-AviTag and SP-6×-HisTag constructs into FreeStyle 293-F Cells at a 1:2 ratio. Transfected cells were cultured in FreeStyle 293 Medium for 3 days and recombinant SP trimers were purified from culture supernatant by FPLC using Nickel-affinity chromatography. Purified proteins were biotinylated in vitro using BirA enzyme.

In terms of the CoV Spike (SP) ectodomains, it is contemplated that SARS1-CoV Spike ectodomain (S SP) with AVI tag has at least about 80%, at least 85%, at least 90%, at least 95%, at least 99%, or 100% sequence identity to the polypeptide of SEQ ID NO:8. The S SP 6His protein is contemplated to have at least about 80%, at least 85%, at least 90%, at least 95%, at least 99%, or 100% sequence identity to the polypeptide of SEQ ID NO:9. The SARS-CoV2 Spike ectodomain (C SP) with AVI tag is contemplated to have at least about 80%, at least 85%, at least 90%, at least 95%, at least 99%, or 100% sequence identity to the polypeptide of SEQ ID NO:10. The C SP 6 His tag protein is contemplated to have at least about 80%, at least 85%, at least 90%, at least 95%, at least 99%, or 100% sequence identity to the polypeptide of SEQ ID NO:11. The MERS Spike ectodomain (M SP) 6His tag protein is contemplated to have at least about 80%, at least 85%, at least 90%, at least 95%, at least 99%, or 100% sequence identity to the polypeptide of SEQ ID NO:12. The M SP AVI Tag protein is contemplated to have at least about 80%, at least 85%, at least 90%, at least 95%, at least 99%, or 100% sequence identity to the polypeptide of SEQ ID NO:13. The OC43 Spike ectodomain (O SP) 6His tag protein is contemplated to have at least about 80%, at least 85%, at least 90%, at least 95%, at least 99%, or 100% sequence identity to the polypeptide of SEQ ID NO:14. The OC43 Spike ectodomain (O SP) 6His tag protein is contemplated to have at least about 80%, at least 85%, at least 90%, at least 95%, at least 99%, or 100% sequence identity to the polypeptide of SEQ ID NO:15. The HKU1 Spike ectodomain (H SP) 6His tag protein is contemplated to have at least about 80%, at least 85%, at least 90%, at least 95%, at least 99%, or 100% sequence identity to the polypeptide of SEQ ID NO:16. The H SP Avi Tag protein is contemplated to have at least about 80%, at least 85%, at least 90%, at least 95%, at least 99%, or 100% sequence identity to the polypeptide of SEQ ID NO:17.

Production of S subdomains: NTD (SARS-CoV-2 $S_{14-305}$) and RBD (SARS-CoV-2 $S_{319-541}$) monomers with a C-terminal dual AviTag/6×-HisTag sequence were produced by transfecting single constructs into FreeStyle 293-F Cells. Following a 3-day expression, subdomains were purified from culture supernatant by FPLC using nickel-affinity chromatography and biotinylated in vitro by addition of BirA.

In terms of the Spike subdomains, it is contemplated that Sars-CoV-2 receptor binding domain (C RBD) 6HIS with AVI tag has at least about 80%, at least 85%, at least 90%, at least 95%, at least 99%, or 100% sequence identity to the polypeptide of SEQ ID NO:18. The Sars-CoV-2 N-terminal domain (C NTD) is contemplated to have at least about 80%, at least 85%, at least 90%, at least 95%, at least 99%, or 100% sequence identity to the polypeptide of SEQ ID NO:19. The SARS1-CoV Receptor binding domain (S RBD) 6HIS AVI tag protein is contemplated to have at least about 80%, at least 85%, at least 90%, at least 95%, at least 99%, or 100% sequence identity to the polypeptide of SEQ ID NO:20.

Production of CoV nucleocapsid protein (N): Recombinant N containing the full-length N and tandem AviTag/6x-HisTag sequence were produced by co-transforming Rosetta cells with the N expression plasmid and an inducible BirA expression plasmid. Cells were grown in the presence of chloramphenicol, ampicillin, and streptomycin, induced with IPTG and supplemented with biotin. Biotinylated N protein was purified by FPLC using a nickel-affinity column and subsequent size exclusion chromatography.

For the N proteins, it is contemplated that the SARS-CoV Nucleocapsid protein (S NP) 6HIS AVI tag has at least about 80%, at least 85%, at least 90%, at least 95%, at least 99%, or 100% sequence identity to the polypeptide of SEQ ID NO:21. The SARS-CoV-2 Nucleocapsid protein (C NP) 6HIS AVI tag is contemplated to have at least about 80%, at least 85%, at least 90%, at least 95%, at least 99%, or 100% sequence identity to the polypeptide of SEQ ID NO:22. The MERS Nucleocapsid protein (M NP) 6HIS AVI tag is contemplated to have at least about 80%, at least 85%, at least 90%, at least 95%, at least 99%, or 100% sequence identity to the polypeptide of SEQ ID NO:23. The OC43 Nucleocapsid protein (O NP) 6HIS AVI tag is contemplated to have at least about 80%, at least 85%, at least 90%, at least 95%, at least 99%, or 100% sequence identity to the polypeptide of SEQ ID NO:24. The HKU1 Nucleocapsid protein (H NP) 6HIS AVI tag is contemplated to have at least about 80%, at least 85%, at least 90%, at least 95%, at least 99%, or 100% sequence identity to the polypeptide of SEQ ID NO:25.

Antibodies and standards: Detection of IG fluorescent goat polyclonal anti-IG F(ab')2 secondaries, SouthernBiotech (IgM cat 2022-02, IgG cat #2062-09, IgA cat #2052-09) Isotype standards were generated by performing the array on mixtures of IG capture beads with 0.75× serial dilutions of purified human antibodies southern biotech (IgG cat #0150-01, IgM Cat#0158L-01, IgA cat #0155L-01) in ranging from 1 ug/mL to 1.3 ng/mL.

Example 4: CBA Assay

Serum samples were diluted into PBS (1/150 for IgG detection, or 1/500 for IgM and IgA detection) and arrayed in 96 well u-bottom plates. A 5 μl suspension containing 5×1e5 of each antigen coated microparticles was added to the samples. In the case of Ig standards, anti-IgM, anti-IgA, and anti-IgG beads were added to 50 ml of the serial dilutions of standard Abs. The suspensions were mixed by pipetting and incubated for 15 min at room temperature. The beads were washed by the addition of 200 μl of PBS and centrifugation at 3000 g for 5 min at room temperature. The CBA particles were resuspended in a secondary staining solution consisting of the appropriate secondary diluted 1/400 in 1% BSA in PBS. The suspension was incubated for 15 min in the dark at room temperature. The beads were washed by the addition of 200 μl of PBS and pelleted by centrifugation at 3000 g for 5 min at room temperature. The particles were resuspended in 80 μl PBS and directly analyzed on a BD Cytoflex flow cytometer in plate mode at sample rate of 100 ml per minute. Sample collection was stopped following the acquisition of 75 μL. Following acquisition, the resulting FCS files were processed using the software described below.

Example 5: Sample Analysis

FCS processing: FCS files derived from the samples were analyzed using a custom software to automatically process FCS files to rapidly quantify the antibody reactivities of serum samples. This software was developed in Matlab (The Mathworks, Inc. Natick MA, USA) version R2020a on MacOS. It requires the Statistics and Machine Learning Toolbox, the Curve Fitting Toolbox and the Signal Processing Toolbox, and additional code from Matlab Central (www.mathworks.com/matlabcentral/).

Concentration determinations: The MFI data are extracted from an FCS file and transformed using the hyperbolic arcsine. Next, a forward-scatter vs. side-scatter plot is used to differentiate the different sized beads and intensity in the APC-cy7 channels as densities of points. These are automatically detected and events within these gates are annotated as distinct populations of beads. Finally, events from each bead gate are evaluated on the secondary isotype flow channel(s) r each bead feature and isotype.

Standard samples for each isotype and bead size are processed similarly and the resulting data are used to compute a four-parameter logistic (4PL) fit for each bead size/isotype/dilution. Finally, the 4PL fits are used to back-calculate concentration units for the MFI data, across the entire data set as a single, tabular text file containing the calculated Ig concentration data for all features in the array.

In some embodiments, the numbers expressing quantities of ingredients, properties such as concentration, reaction conditions, and so forth, used to describe and claim certain embodiments of the invention are to be understood as being modified in some instances by the term “about.” Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term “administering” a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms “prognosing” or “predicting” a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A vaccine composition for eliciting in a subject an immune response against SARS-COV-2 or a variant thereof, the composition comprising 1) a first vaccine for administration as a prime vaccination, the first vaccine comprising an RNA vaccine comprising a ribonucleic acid encoding a severe acute respiratory syndrome (SARS) coronavirus spike protein (S), and 2) a second vaccine for administration as a boost vaccination, the second vaccine comprising a recombinant adenovirus comprising a first and second nucleic acid, wherein the first nucleic acid encodes a SARS coronavirus nucleocapsid protein (N) that is fused to an endosomal targeting sequence (N-ETSD), wherein the first nucleic acid encodes the amino acid sequence of SEQ ID NO: 1 or SEQ ID NO:7; and wherein the second nucleic acid encodes a SARS coronavirus spike protein (S).

2. The vaccine composition of claim 1, wherein the immune response comprises the generation of antibodies that bind to the Delta, Omicron, Wuhan, Alpha, Epsilon, Gamma, and Beta variants of SARS-Co V2.

3. The vaccine composition of claim 1, wherein the immune response is generation of cytotoxic T cells that have cytotoxicity against different cells harboring Delta, Omicron, Wuhan, Alpha, Epsilon, Gamma, or Beta variants of SARS-Co V2.

4. The vaccine composition of claim 1, wherein the immune response is generation of memory T cells and/or memory B cells.

5. The vaccine composition of claim 1, wherein the endosomal targeting sequence of the N-ETSD is encoded at a 5'-end of the first nucleic acid and/or wherein the endosomal targeting sequence of the N-ETSD is encoded at a 3'-end of the first nucleic acid.

6. The vaccine composition of claim 1, wherein the first and second nucleic acids are arranged in a bicistronic sequence.

7. The vaccine composition of claim 1, wherein the first nucleic acid has the nucleotide sequence of SEQ ID NO:2.

8. The vaccine composition of claim 1, wherein the S protein has the amino acid sequence of SEQ ID NO:3 or SEQ ID NO:4.

9. The vaccine composition of claim 1, wherein the second nucleic acid has the nucleotide sequence of SEQ ID NO:5 or SEQ ID NO:6.

10. The vaccine composition of claim 1, wherein the recombinant adenovirus comprises an E1 gene region deletion and an E2b gene region deletion.

11. The vaccine composition of claim 1, wherein the vaccine composition is formulated for administration in an amount that elicits the immune response.

12. The vaccine composition of claim 1, wherein the RNA vaccine comprises a self-amplifying and self-adjuvanted RNA vaccine.

13. The vaccine composition of claim 12, wherein the self-amplifying and self-adjuvanted RNA vaccine is coupled to a lipid carrier.

14. A vaccine composition for generating memory T cells having specificity for SARS-COV2 or a variant thereof, the composition comprising 1) a first vaccine for administration as a prime vaccination, the first vaccine comprising a self-amplifying RNA vaccine comprising a ribonucleic acid encoding a severe acute respiratory syndrome (SARS) coronavirus spike protein (S), and 2) a second vaccine for administration as a boost vaccination, the second vaccine comprising a recombinant adenovirus comprising a first and second nucleic acid, wherein the first nucleic acid encodes a SARS coronavirus nucleocapsid protein (N) that is fused to an endosomal targeting sequence (N-ETSD), wherein the first nucleic acid encodes the amino acid sequence of SEQ ID NO: 1 or SEQ ID NO:7; and wherein the second nucleic acid encodes a SARS coronavirus spike protein (S).

15. The vaccine composition of claim 6, wherein the memory T cells have specificity for the Delta, Omicron, Wuhan, Alpha, Epsilon, Gamma, and Beta variants of SARS-COV2.

16. A kit for eliciting in a subject an immune response against SARS-COV-2 or a variant thereof, the kit comprising 1) a first vaccine for administration as a prime vaccination composition, the first vaccine comprising a self-amplifying RNA vaccine comprising a ribonucleic acid encoding a severe acute respiratory syndrome (SARS) coronavirus spike protein (S), and 2) a second vaccine for administration as a boost vaccination composition, the second vaccine comprising a recombinant adenovirus comprising a first and second nucleic acid, wherein the first nucleic acid encodes a SARS coronavirus nucleocapsid protein (N) that is fused to an endosomal targeting sequence (N-ETSD), wherein the first nucleic acid encodes the amino acid sequence of SEQ ID NO:1 or SEQ ID NO:7; and wherein the second nucleic acid encodes a SARS coronavirus spike protein (S).

* * * * *

SEQUENCE LISTING

```
Sequence total quantity: 26
SEQ ID NO: 1            moltype = AA  length = 516
FEATURE                 Location/Qualifiers
REGION                  1..516
                        note = SARS-CoV2 Nucleocapsid protein tagged with ETSD
                         signal
source                  1..516
                        mol_type = protein
                        organism = synthetic construct
SEQUENCE: 1
MLLLPFQLLA VLFPGGNSED YKDDDDKGGG SGGGSGGGSG GGSMSDNGPQ NQRNAPRITF  60
GGPSDSTGSN QNGERSGARS KQRRPQGLPN NTASWFTALT QHGKEDLKFP RGQGVPINTN  120
SSPDDQIGYY RRATRRIRGG DGKMKDLSPR WYFYYLGTGP EAGLPYGANK DGIIWVATEG  180
ALNTPKDHIG TRNPANNAAI VLQLPQGTTL PKGFYAEGSR GGSQASSRSS SRSRNSSRNS  240
TPGSSRGTSP ARMAGNGGDA ALALLLLDRL NQLESKMSGK GQQQQGQTVT KKSAAEASKK  300
PRQKRTATKA YNVTQAFGRR GPEQTQGNFG DQELIRQGTD YKHWPQIAQF APSASAFFGM  360
SRIGMEVTPS GTWLTYTGAI KLDDKDPNFK DQVILLNKHI DAYKTFPPTE PKKDKKKKAD  420
ETQALPQRQK KQQTVTLLPA ADLDDFSKQL QQSMSSADST QAGPGPGNLV PMVATVGPGP  480
GMLIPIAVGG ALAGLVLIVL IAYLIGKKHC SYQDIL                            516

SEQ ID NO: 2            moltype = DNA  length = 1551
FEATURE                 Location/Qualifiers
misc_feature            1..1551
                        note = SARS-CoV2 nucleocapsid tagged with ETSD
source                  1..1551
                        mol_type = other DNA
                        organism = synthetic construct
SEQUENCE: 2
atgctgctgc tgcccttcca gttgctggct gtcctctttc ccggcggcaa ctccgaggat  60
tacaaggacg acgacgacaa gggtggaggc tctggaggtg gctctggtgg aggttccggt  120
ggcggatcta tgagcgacaa cggtccccag aatcaaagaa atgcgcccag aattacattc  180
ggcggccctt ctgatagcac tggctcaaat caaaacgggg agagaagcgg agccaggtcc  240
aaacagcgga gaccccaagg cctgcctaat aacaccgctt cctggttcac agctctgacg  300
caacacggca aggaggatct gaagtttcca cggggtcagg gcgtcccgat taacacgaac  360
tctagcccag atgaccaaat agggtactac agaagagcga caaggcggat cagaggaggc  420
gatggaaaaa tgaaggatct gtcccctagg tggtatttct attacctggg cacaggccct  480
gaagctgggt tgccttacgg cgcaaacaaa gatggaatta tatgggtggc caccgagggg  540
gcgttgaaca ccccaaagga tcacatcgga acgaggaatc ccgccaacaa tgctgctata  600
gtgctccaac tgccacaggg aacaaccctg cctaagggct tctacgccga ggggagccgc  660
ggtggcagcc aggccagctc cagaagttcc tcccgcagcc ggaacagctc tagaaacagc  720
actcccggca gctccagagg gacaagccca gccagaatgg ccggcaatgg cggcgacgct  780
gccctcgcac ttctgttgct tgatcggctc aatcaactcg aaagcaaaat gtccggcaag  840
ggacaacaac agcaaggaca gaccgttaca aaaaaaagcg ccgccgaggc tagcaagaag  900
cccagacaga agcgaaccgc aacaaaggcc tataatgtaa cacaagcctt tggaaggcgg  960
ggacccgaac agacccaggg aaattttggc gaccaggaac tgatccggca agggacagac  1020
tataaacatt ggccacagat agcgcaattt gctccctccg cctccgcctt ctttggcatg  1080
tcaagaatag gcatggaagt aactccttct ggaacctggc tgacgtacac tggggcaatc  1140
aagttggatg ataaggaccc taatttcaag gaccaagtta ttttgctcaa caagcatata  1200
gacgcctaca agactttccc gcctaccgaa cctaaaaagg ataagaagaa gaaagcagac  1260
gagacccagg ccctgcctca acggcaaaag aagcagcaaa ctgtgacact cctgcccgcc  1320
```

-continued

```
gctgacttgg atgatttttc aaaacagctc caacagagta tgagcagcgc cgatagcacc  1380
caagctggac cgggtccggg caacctggtg ccgatggtgg cgaccgtggg tccaggaccg  1440
ggtatgctga tccccatcgc cgtgggcggg gccctggccg gcctcgtgct gatcgtcctt  1500
atcgcctacc tcatcggcaa gaagcactgc tcatatcagg acatcctgtg a           1551

SEQ ID NO: 3            moltype = AA  length = 1282
FEATURE                 Location/Qualifiers
REGION                  1..1282
                        note = SARS-CoV2 spike protein with HA tag
source                  1..1282
                        mol_type = protein
                        organism = synthetic construct
SEQUENCE: 3
MFVFLVLLPL VSSYPYDVPD YAQCVNLTTR TQLPPAYTNS FTRGVYYPDK VFRSSVLHST  60
QDLFLPFFSN VTWFHAIHVS GTNGTKRFDN PVLPFNDGVY FASTEKSNII RGWIFGTTLD  120
SKTQSLLIVN NATNVVIKVC EFQFCNDPFL GVYYHKNNKS WMESEFRVYS SANNCTFEYV  180
SQPFLMDLEG KQGNFKNLRE FVFKNIDGYF KIYSKHTPIN LVRDLPQGFS ALEPLVDLPI  240
GINITRFQTL LALHRSYLTP GDSSSGWTAG AAAYYVGYLQ PRTFLLKYNE NGTITDAVDC  300
ALDPLSETKC TLKSFTVEKG IYQTSNFRVQ PTESIVRFPN ITNLCPFGEV FNATRFASVY  360
AWNRKRISNC VADYSVLYNS ASFSTFKCYG VSPTKLNDLC FTNVYADSFV IRGDEVRQIA  420
PGQTGKIADY NYKLPDDFTG CVIAWNSNNL DSKVGGNYNY LYRLFRKSNL KPFERDISTE  480
IYQAGSTPCN GVEGFNCYFP LQSYGFQPTN GVGYQPYRVV VLSFELLHAP ATVCGPKKST  540
NLVKNKCVNF NFNGLTGTGV LTESNKKFLP FQQFGRDIAD TTDAVRDPQT LEILDITPCS  600
FGGVSVITPG TNTSNQVAVL YQDVNCTEVP VAIHADQLTP TWRVYSTGSN VFQTRAGCLI  660
GAEHVNNSYE CDIPIGAGIC ASYQTQTNSP RRARSVASQS IIAYTMSLGA ENSVAYSNNS  720
IAIPTNFTIS VTTEILPVSM TKTSVDCTMY ICGDSTECSN LLLQYGSFCT QLNRALTGIA  780
VEQDKNTQEV FAQVKQIYKT PPIKDFGGFN FSQILPDPSK PSKRSFIEDL LFNKVTLADA  840
GFIKQYGDCL GDIAARDLIC AQKFNGLTVL PPLLTDEMIA QYTSALLAGT ITSGWTFGAG  900
AALQIPFAMQ MAYRFNGIGV TQNVLYENQK LIANQFNSAI GKIQDSLSST ASALGKLQDV  960
VNQNAQALNT LVKQLSSNFG AISSVLNDIL SRLDKVEAEV QIDRLITGRL QSLQTYVTQQ  1020
LIRAAEIRAS ANLAATKMSE CVLGQSKRVD FCGKGYHLMS FPQSAPHGVV FLHVTYVPAQ  1080
EKNFTTAPAI CHDGKAHFPR EGVFVSNGTH WFVTQRNFYE PQIITTDNTF VSGNCDVVIG  1140
IVNNTVYDPL QPELDSFKEE LDKYFKNHTS PDVDLGDISG INASVVNIQK EIDRLNEVAK  1200
NLNESLIDLQ ELGKYEQYIK WPWYIWLGFI AGLIAIVMVT IMLCCMTSCC SCLKGCCSCG  1260
SCCKFDEDDS EPVLKGVKLH YT                                          1282

SEQ ID NO: 4            moltype = AA  length = 1298
FEATURE                 Location/Qualifiers
REGION                  1..1298
                        note = SARS-CoV2 spike protein optimized for surface
                         expression ("Sfusion")
source                  1..1298
                        mol_type = protein
                        organism = synthetic construct
SEQUENCE: 4
MFVFLVLLPL VSSYPYDVPD YAGGGSGGGS GGGSGGGSQC VNLTTRTQLP PAYTNSFTRG  60
VYYPDKVFRS SVLHSTQDLF LPFFSNVTWF HAIHVSGTNG TKRFDNPVLP FNDGVYFAST  120
EKSNIIRGWI FGTTLDSKTQ SLLIVNNATN VVIKVCEFQF CNDPFLGVYY HKNNKSWMES  180
EFRVYSSANN CTFEYVSQPF LMDLEGKQGN FKNLREFVFK NIDGYFKIYS KHTPINLVRD  240
LPQGFSALEP LVDLPIGINI TRFQTLLALH RSYLTPGDSS SGWTAGAAAY YVGYLQPRTF  300
LLKYNENGTI TDAVDCALDP LSETKCTLKS FTVEKGIYQT SNFRVQPTES IVRFPNITNL  360
CPFGEVFNAT RFASVYAWNR KRISNCVADY SVLYNSASFS TFKCYGVSPT KLNDLCFTNV  420
YADSFVIRGD EVRQIAPGQT GKIADYNYKL PDDFTGCVIA WNSNNLDSKV GGNYNYLYRL  480
FRKSNLKPFE RDISTEIYQA GSTPCNGVEG FNCYFPLQSY GFQPTNGVGY QPYRVVVLSF  540
ELLHAPATVC GPKKSTNLVK NKCVNFNFNG LTGTGVLTES NKKFLPFQQF GRDIADTTDA  600
VRDPQTLEIL DITPCSFGGV SVITPGTNTS NQVAVLYQDV NCTEVPVAIH ADQLTPTWRV  660
YSTGSNVFQT RAGCLIGAEH VNNSYECDIP IGAGICASYQ TQTNSPRRAR SVASQSIIAY  720
TMSLGAENSV AYSNNSIAIP TNFTISVTTE ILPVSMTKTS VDCTMYICGD STECSNLLLQ  780
YGSFCTQLNR ALTGIAVEQD KNTQEVFAQV KQIYKTPPIK DFGGFNFSQI LPDPSKPSKR  840
SFIEDLLFNK VTLADAGFIK QYGDCLGDIA ARDLICAQKF NGLTVLPPLL TDEMIAQYTS  900
ALLAGTITSG WTFGAGAALQ IPFAMQMAYR FNGIGVTQNV LYENQKLIAN QFNSAIGKIQ  960
DSLSSTASAL GKLQDVVNQN AQALNTLVKQ LSSNFGAISS VLNDILSRLD KVEAEVQIDR  1020
LITGRLQSLQ TYVTQQLIRA AEIRASANLA ATKMSECVLG QSKRVDFCGK GYHLMSFPQS  1080
APHGVVFLHV TYVPAQEKNF TTAPAICHDG KAHFPREGVF VSNGTHWFVT QRNFYEPQII  1140
TTDNTFVSGN CDVVIGIVNN TVYDPLQPEL DSFKEELDKY FKNHTSPDVD LGDISGINAS  1200
VVNIQKEIDR LNEVAKNLNE SLIDLQELGK YEQYIKWPWY IWLGFIAGLI AIVMVTIMLC  1260
CMTSCCSCLK GCCSCGSCCK FDEDDSEPVL KGVKLHYT                          1298

SEQ ID NO: 5            moltype = DNA  length = 3849
FEATURE                 Location/Qualifiers
misc_feature            1..3849
                        note = SARS-CoV2 spike protein with HA tag
source                  1..3849
                        mol_type = other DNA
                        organism = synthetic construct
SEQUENCE: 5
atgttcgttt ttctcgttct cctcccgctt gtgagcagct atccgtatga tgtgccggat  60
tatgcgcaat gtgtcaacct caccacaagg acacagctcc ctcccgcata tacgaatagc  120
tttaccagag gcgtatacta tcctgataag gtctttagga gctcagtact gcatagcact  180
```

-continued

```
caggatctct tcctgccgtt cttcagtaat gttacttggt ttcacgccat tcatgtttcc  240
gggaccaatg gcaccaaacg gttcgataat ccagtgcttc ccttcaacga tggggtgtac  300
tttgccagca ctgaaaaatc taatataatt cggggatgga ttttcggaac cacactcgat  360
tccaagactc agtccctctt gatcgttaac aacgctacta atgttgtcat taaggtgtgt  420
gagtttcagt tctgcaacga ccctttcctg ggtgtctact accataaaaa taacaagagc  480
tggatggagt ccgaatttcg cgtctactca agcgccaata attgcacttt tgagtatgtg  540
tcccagccct ttttgatgga tctggaggga aagcagggca atttcaaaaa tctgagagaa  600
ttcgttttta agaatataga tggatacttc aaaatctaca gcaaacacac acccataaat  660
cttgtgcgcg atcttcccca gggcttcagc gcgttggaac cccttgttga cttgcccata  720
ggcatcaaca ttaccaggtt ccaaacgctg ctcgccctcc accgcagcta cttgacaccc  780
ggggattcca gctccggatg gaccgccggc gccgcagcgt attatgtggg gtacctgcaa  840
cccaggacat ttttgctcaa gtacaatgag aatgggacca tcacagatgc ggtagactgt  900
gcactggatc cactcagcga aactaaatgt accctgaaaa gctttaccgt ggagaaagga  960
atctaccaaa ccagcaactt cagggtccag cccactgaat ccatcgttag atttccaaat  1020
ataactaatt tgtgtccatt tggagaggtg ttcaatgcta caaggttcgc gtctgtatac  1080
gcttggaacc ggaagcgcat ctcaaattgc gtggctgatt atagcgttct ttacaacagc  1140
gcttcctttt ccacgttcaa gtgctatggt gtatccccga caaagctgaa tgacttgtgc  1200
ttcaccaatg tgtatgcgga ttctttcgtt attcgaggcg atgaagtcag acaaattgcg  1260
cctggccaga ccggaaagat tgccgactac aactataaac tgccggacga ctttactggt  1320
tgcgtgatcg cttggaacag caataatctt gatagtaaag ttggaggaaa ctacaattac  1380
ctctatagac tgttcagaaa gagcaacttg aagccattcg aacgggatat ctctacggag  1440
atctatcaag ctggcagcac cccctgcaat ggtgtggaag gctttaattg ttatttttcct  1500
ttgcagagct atggcttcca acctaccaac ggagtgggct accagcccta cagagtggtg  1560
gtgctcagct ttgaactgct gcatgccccg gccacagttt gcgggcccaa aaaaagcacg  1620
aatctggtta agaacaaatg cgtcaacttc aattttaatg ggttgacagg tacaggcgta  1680
ctgaccgaat ccaacaaaaa gttcctgcct tttcagcagt tcgggagaga tatcgccgac  1740
actacagacg ccgtcaggga tccccaaaca ctcgaaattc tggacatcac accttgttcc  1800
ttcggcgggg tatctgtgat tactccgggc acaaatacca gtaaccaggt agcggtgctt  1860
taccaggatg tcaactgtac ggaagtacct gtcgctattc atgcggatca actcactcct  1920
acctggagag tttattccac tgggtccaac gtgtttcaga cccgagccgg ctgcttgatt  1980
ggcgcggaac atgttaacaa ctcctacgaa tgtgacatcc ctatcggagc tggcatctgt  2040
gcttcctatc aaacgcaaac gaacagccca cggcgggcca gatccgtagc ctctcaaagc  2100
atcatcgctt atactatgtc cttgggggct gaaaacagcg ttgcctattc caacaatagc  2160
atcgctatcc ctaccaactt taccatttcc gtgaccacag aaatactgcc ggtgagcatg  2220
acaaagactt ctgtggactg taccatgtat atatgcggcg atagcacaga gtgttctaat  2280
ttgctgctgc agtacggcag cttttgtacc caactcaaca gagcacttac agggattgcc  2340
gtcgagcagg ataaaaacac ccaggaggtt ttcgcccagg ttaagcagat ctacaagacc  2400
ccaccaatca aggatttcgg cggcttcaat ttttcccaga tactgcccga tccttccaag  2460
ccatccaaaa ggagctttat agaggatctg ctgttcaaca aggtgactct ggccgacgct  2520
ggctttatca agcaatatgg cgattgcctg ggggatattg ccgctaggga ccttatctgc  2580
gctcaaaaat tcaacggtct taccgttctc ccgcccctgc tcaccgacga gatgatagcc  2640
cagtacacga gcgcactttt ggccggcacg ataaccagcg gctggacatt cggtgccggg  2700
gccgctcttc aaatcccctt tgccatgcag atggcctaca gatttaatgg gataggcgtg  2760
acacaaaatg tcttgtatga aaatcagaaa ctgattgcaa accagtttaa tagcgctatt  2820
ggcaagatcc aagatagcct ttcctccacc gcatccgctc tgggaaagtt gcaagacgtc  2880
gtgaatcaaa acgcccaagc tctgaatacc ctcgtgaagc agcttagctc caactttggc  2940
gcgatatcct ccgtgctgaa cgatatcctg tccagattgg acaaggtcga ggcagaagtc  3000
cagatcgata gattgataac cggcagactc cagtctctgc agacatatgt gactcagcag  3060
ttgataagag cggccgaaat acgagcgtct gcaaatctcg cagcaacgaa aatgtcagag  3120
tgtgtattgg ggcaaagtaa aagagtagat ttctgtggaa agggttacca tctgatgtca  3180
ttcccccagt ctgcaccaca tggagtagtt tttttgcatg tgacttatgt gcctgcccag  3240
gagaaaaatt tcaccactgc acctgcgatc tgtcatgacg gcaaggcaca tttccctaga  3300
gaaggcgtct tcgtatcaaa tggaacacac tggtttgtaa cccaaaggaa cttttacgag  3360
ccccaaatta taactaccga caacaccttc gtaagcggaa actgcgacgt cgttataggg  3420
atagtcaata atacggtcta tgaccctctt cagccggaac tggactcctt taaagaagaa  3480
ctggataagt acttcaagaa ccatacgtct ccggatgtgg atctcggaga tataagtgga  3540
atcaacgcaa gcgtagtaaa cattcagaag gagatagacc gactcaatga ggttgctaaa  3600
aacctgaacg aaagcttgat agacttgcag gagctgggta agtacgaaca gtacattaag  3660
tggccatggt atatctggtt gggcttcata gcaggactca tagctatcgt catggtgaca  3720
ataatgcttt gttgtatgac cagctgttgt tcttgtctga aaggctgctg cagctgtggc  3780
agctgttgta aatttgacga agatgattcc gagcctgtgc ttaagggcgt aaaactccac  3840
tatacatga                                                    3849
```

```
SEQ ID NO: 6          moltype = DNA  length = 3897
FEATURE               Location/Qualifiers
misc_feature          1..3897
                      note = SARS-CoV2 spike protein optimized for surface
                       expression ("Sfusion")
source                1..3897
                      mol_type = other DNA
                      organism = synthetic construct
SEQUENCE: 6
atgttcgttt ttctcgttct cctcccgctt gtgagcagct atccgtatga tgtgccggat  60
tatgcgggtg gaggctctgg aggtggctct ggtggaggtt ccggtggcgg atctcaatgt  120
gtcaacctca ccacaaggac acagctccct cccgcatata cgaatagctt taccagaggc  180
gtatactatc ctgataaggt ctttaggagc tcagtactgc atagcactca ggatctcttc  240
ctgccgttct tcagtaatgt tacttggttt cacgccattc atgtttccgg gaccaatggc  300
accaaacggt tcgataatcc agtgcttccc ttcaacgatg ggtgtactt tgccagcact  360
gaaaaatcta atataattcg gggatggatt ttcggaacca cactcgattc caagactcag  420
```

-continued

```
tccctcttga tcgttaacaa cgctactaat gttgtcatta aggtgtgtga gtttcagttc  480
tgcaacgacc ctttcctggg tgtctactac cataaaaata acaagagctg gatggagtcc  540
gaatttcgcg tctactcaag cgccaataat tgcacttttg agtatgtgtc ccagcccttt  600
ttgatggatc tggagggaaa gcagggcaat ttcaaaaatc tgagagaatt cgtttttaag  660
aatatagatg gatacttcaa aatctacagc aaacacacac ccataaatct tgtgcgcgat  720
cttccccagg gcttcagcgc gttggaaccc cttgttgact tgcccatagg catcaacatt  780
accaggttcc aaacgctgct cgccctccac cgcagctact tgacacccgg ggattccagc  840
tccggatgga ccgccggcgc cgcagcgtat tatgtggggt acctgcaacc caggacattt  900
ttgctcaagt acaatgagaa tgggaccatc acagatgcgg tagactgtgc actggatcca  960
ctcagcgaaa ctaaatgtac cctgaaaagc tttaccgtgg agaaaggaat ctaccaaacc  1020
agcaacttca gggtccagcc cactgaatcc atcgttagat ttccaaatat aactaatttg  1080
tgtccatttg gagaggtgtt caatgctaca aggttcgcgt ctgtatacgc ttggaaccgg  1140
aagcgcatct caaattgcgt ggctgattat agcgttcttt acaacagcgc ttccttttcc  1200
acgttcaagt gctatggtgt atccccgaca aagctgaatg acttgtgctt caccaatgtg  1260
tatgcggatt ctttcgttat tcgaggcgat gaagtcagac aaattgcgcc tggccagacc  1320
ggaaagattg ccgactacaa ctataaactg ccggacgact ttactggttg cgtgatcgct  1380
tggaacagca ataatcttga tagtaaagtt ggaggaaact acaattacct ctatagactg  1440
ttcagaaaga gcaacttgaa gccattcgaa cgggatatct ctacggagat ctatcaagct  1500
ggcagcaccc cctgcaatgg tgtggaaggc tttaattgtt attttccttt gcagagctat  1560
ggcttccaac ctaccaacgg agtgggctac cagccctaca gagtggtggt gctcagcttt  1620
gaactgctgc atgccccggc cacagtttgc gggcccaaaa aaagcacgaa tctggttaag  1680
aacaaatgcg tcaacttcaa ttttaatggg ttgacaggta caggcgtact gaccgaatcc  1740
aacaaaaagt tcctgccttt tcagcagttc gggagagata tcgccgacac tacagacgcc  1800
gtcagggatc cccaaacact cgaaattctg gacatcacac cttgttcctt cggcggggta  1860
tctgtgatta ctccgggcac aaataccagt aaccaggtag cggtgcttta ccaggatgtc  1920
aactgtacgg aagtacctgt cgctattcat gcggatcaac tcactcctac ctggagagtt  1980
tattccactg ggtccaacgt gtttcagacc cgagccggct gcttgattgg cgcggaacat  2040
gttaacaact cctacgaatg tgacatccct atcggagctg gcatctgtgc ttcctatcaa  2100
acgcaaacga acagcccacg gcgggccaga tccgtagcct ctcaaagcat catcgcttat  2160
actatgtcct tgggggctga aaacagcgtt gcctattcca acaatagcat cgctatccct  2220
accaacttta ccatttccgt gaccacagaa atactgccgg tgagcatgac aaagacttct  2280
gtggactgta ccatgtatat atgcggcgat agcacagagt gttctaattt gctgctgcag  2340
tacggcagct tttgtaccca actcaacaga gcacttacag ggattgccgt cgagcaggat  2400
aaaaacaccc aggaggtttt cgcccaggtt aagcagatct acaagacccc accaatcaag  2460
gatttcggcg gcttcaattt ttcccagata ctgcccgatc cttccaagcc atccaaaagg  2520
agctttatag aggatctgct gttcaacaag gtgactctgg ccgacgctgg ctttatcaag  2580
caatatggcg attgcctggg ggatattgcc gctagggacc ttatctgcgc tcaaaaattc  2640
aacggtctta ccgttctccc gcccctgctc accgacgaga tgatagccca gtacacgagc  2700
gcacttttgg ccggcacgat aaccagcggc tggacattcg gtgccggggc cgctcttcaa  2760
atcccctttg ccatgcagat ggcctacaga tttaatggga taggcgtgac acaaaatgtc  2820
ttgtatgaaa atcagaaact gattgcaaac cagtttaata gcgctattgg caagatccaa  2880
gatagccttt cctccaccgc atccgctctg ggaaagttgc aagacgtcgt gaatcaaaac  2940
gcccaagctc tgaataccct cgtgaagcag cttagctcca actttggcgc gatatcctcc  3000
gtgctgaacg atatcctgtc cagattggac aaggtcgagg cagaagtcca gatcgataga  3060
ttgataaccg gcagactcca gtctctgcag acatatgtga ctcagcagtt gataagagcg  3120
gccgaaatac gagcgtctgc aaatctcgca gcaacgaaaa tgtcagagtg tgtattgggg  3180
caaagtaaaa gagtagattt ctgtggaaag ggttaccatc tgatgtcatt cccccagtct  3240
gcaccacatg gagtagtttt tttgcatgtg acttatgtgc ctgcccagga gaaaaatttc  3300
accactgcac ctgcgatctg tcatgacggc aaggcacatt tccctagaga aggcgtcttc  3360
gtatcaaatg gaacacactg gtttgtaacc caaaggaact tttacgagcc ccaaattata  3420
actaccgaca acaccttcgt aagcggaaac tgcgacgtcg ttatagggat agtcaataat  3480
acggtctatg accctcttca gccggaactg gactccttta aagaagaact ggataagtac  3540
ttcaagaacc atacgtctcc ggatgtggat ctcggagata taagtggaat caacgcaagc  3600
gtagtaaaca ttcagaagga gatagaccga ctcaatgagg ttgctaaaaa cctgaacgaa  3660
agcttgatag acttgcagga gctgggtaag tacgaacagt acattaagtg gccatggtat  3720
atctggttgg gcttcatagc aggactcata gctatcgtca tggtgacaat aatgctttgt  3780
tgtatgacca gctgttgttc ttgtctgaaa ggctgctgca gctgtggcag ctgttgtaaa  3840
tttgacgaag atgattccga gcctgtgctt aagggcgtaa aactccacta tacatga     3897
```

```
SEQ ID NO: 7            moltype = AA  length = 473
FEATURE                 Location/Qualifiers
source                  1..473
                        mol_type = protein
                        organism = SARS-CoV2
SEQUENCE: 7
MSDNGPQNQR NAPRITFGGP SDSTGSNQNG ERSGARSKQR RPQGLPNNTA SWFTALTQHG  60
KEDLKFPRGQ GVPINTNSSP DDQIGYYRRA TRRIRGGDGK MKDLSPRWYF YYLGTGPEAG  120
LPYGANKDGI IWVATEGALN TPKDHIGTRN PANNAAIVLQ LPQGTTLPKG FYAEGSRGGS  180
QASSRSSSRS RNSSRNSTPG SSRGTSPARM AGNGGDAALA LLLLDRLNQL ESKMSGKGQQ  240
QQGQTVTKKS AAEASKKPRQ KRTATKAYNV TQAFGRRGPE QTQGNFGDQE LIRQGTDYKH  300
WPQIAQFAPS ASAFFGMSRI GMEVTPSGTW LTYTGAIKLD DKDPNFKDQV ILLNKHIDAY  360
KTFPPTEPKK DKKKKADETQ ALPQRQKKQQ TVTLLPAADL DDFSKQLQQS MSSADSTQAG  420
PGPGNLVPMV ATVGPGPGML IPIAVGGALA GLVLIVLIAY LIGKKHCSYQ DIL         473
```

```
SEQ ID NO: 8            moltype = AA  length = 1249
FEATURE                 Location/Qualifiers
REGION                  1..1249
                        note = SARS1-CoV Spike ectodomain (S SP) AVI tag;
                         Mutations: Furinecleavage, Diproline
```

-continued

```
source                  1..1249
                        mol_type = protein
                        organism = synthetic construct
SEQUENCE: 8
MEFGLSWLFL VAILKGVQCE VSDLDRCTTF DDVQAPNYTQ HTSSMRGVYY PDEIFRSDTL  60
YLTQDLFLPF YSNVTGFHTI NHTFDNPVIP FKDGIYFAAT EKSNVVRGWV FGSTMNNKSQ  120
SVIIINNSTN VVIRACNFEL CDNPFFAVSK PMGTQTHTMI FDNAFNCTFE YISDAFSLDV  180
SEKSGNFKHL REFVFKNKDG FLYVYKGYQP IDVVRDLPSG FNTLKPIFKL PLGINITNFR  240
AILTAFSPAQ DTWGTSAAAY FVGYLKPTTF MLKYDENGTI TDAVDCSQNP LAELKCSVKS  300
FEIDKGIYQT SNFRVVPSGD VVRFPNITNL CPFGEVFNAT KFPSVYAWER KKISNCVADY  360
SVLYNSTFFS TFKCYGVSAT KLNDLCFSNV YADSFVVKGD DVRQIAPGQT GVIADYNYKL  420
PDDFMGCVLA WNTRNIDATS TGNYNYKYRY LRHGKLRPFE RDISNVPFSP DGKPCTPPAL  480
NCYWPLNDYG FYTTTGIGYQ PYRVVVLSFE LLNAPATVCG PKLSTDLIKN QCVNFNFNGL  540
TGTGVLTPSS KRFQPFQQFG RDVSDFTDSV RDPKTSEILD ISPCSFGGVS VITPGTNASS  600
EVAVLYQDVN CTDVSTAIHA DQLTPAWRIY STGNNVFQTQ AGCLIGAEHV DTSYECDIPI  660
GAGICASYHT VSLLRSTSQK SIVAYTMSLG ADSSIAYSNN TIAIPTNFSI SITTEVMPVS  720
MAKTSVDCNM YICGDSTECA NLLLQYGSFC TQLNRALSGI AAEQDRNTRE VFAQVKQMYK  780
TPTLKYFGGF NFSQILPDPL KPTKRSFIED LLFNKVTLAD AGFMKQYGEC LGDINARDLI  840
CAQKFNGLTV LPPLLTDDMI AAYTAALVSG TATAGWTFGA GAALQIPFAM QMAYRFNGIG  900
VTQNVLYENQ KQIANQFNKA ISQIQESLTT TSTALGKLQD VVNQNAQALN TLVKQLSSNF  960
GAISSVLNDI LSRLDPPEAE VQIDRLITGR LQSLQTYVTQ QLIRAAEIRA SANLAATKMS  1020
ECVLGQSKRV DFCGKGYHLM SFPQAAPHGV VFLHVTYVPS QERNFTTAPA ICHEGKAYFP  1080
REGVFVFNGT SWFITQRNFF SPQIITTDNT FVSGNCDVVI GIINNTVYDP LQPELDSFKE  1140
ELDKYFKNHT SPDVDLGDIS GINASVVNIQ KEIDRLNEVA KNLNESLIDL QELGKYEQYI  1200
KGGGSGYIPE APRDGQAYVR KDGEWVLLST FLGSGLNDIF EAQKIEWHE             1249

SEQ ID NO: 9            moltype = AA  length = 1240
FEATURE                 Location/Qualifiers
REGION                  1..1240
                        note = S SP 6His tag; Mutations: Furine cleavage, Diproline
source                  1..1240
                        mol_type = protein
                        organism = synthetic construct
SEQUENCE: 9
MEFGLSWLFL VAILKGVQCE VSDLDRCTTF DDVQAPNYTQ HTSSMRGVYY PDEIFRSDTL  60
YLTQDLFLPF YSNVTGFHTI NHTFDNPVIP FKDGIYFAAT EKSNVVRGWV FGSTMNNKSQ  120
SVIIINNSTN VVIRACNFEL CDNPFFAVSK PMGTQTHTMI FDNAFNCTFE YISDAFSLDV  180
SEKSGNFKHL REFVFKNKDG FLYVYKGYQP IDVVRDLPSG FNTLKPIFKL PLGINITNFR  240
AILTAFSPAQ DTWGTSAAAY FVGYLKPTTF MLKYDENGTI TDAVDCSQNP LAELKCSVKS  300
FEIDKGIYQT SNFRVVPSGD VVRFPNITNL CPFGEVFNAT KFPSVYAWER KKISNCVADY  360
SVLYNSTFFS TFKCYGVSAT KLNDLCFSNV YADSFVVKGD DVRQIAPGQT GVIADYNYKL  420
PDDFMGCVLA WNTRNIDATS TGNYNYKYRY LRHGKLRPFE RDISNVPFSP DGKPCTPPAL  480
NCYWPLNDYG FYTTTGIGYQ PYRVVVLSFE LLNAPATVCG PKLSTDLIKN QCVNFNFNGL  540
TGTGVLTPSS KRFQPFQQFG RDVSDFTDSV RDPKTSEILD ISPCSFGGVS VITPGTNASS  600
EVAVLYQDVN CTDVSTAIHA DQLTPAWRIY STGNNVFQTQ AGCLIGAEHV DTSYECDIPI  660
GAGICASYHT VSLLRSTSQK SIVAYTMSLG ADSSIAYSNN TIAIPTNFSI SITTEVMPVS  720
MAKTSVDCNM YICGDSTECA NLLLQYGSFC TQLNRALSGI AAEQDRNTRE VFAQVKQMYK  780
TPTLKYFGGF NFSQILPDPL KPTKRSFIED LLFNKVTLAD AGFMKQYGEC LGDINARDLI  840
CAQKFNGLTV LPPLLTDDMI AAYTAALVSG TATAGWTFGA GAALQIPFAM QMAYRFNGIG  900
VTQNVLYENQ KQIANQFNKA ISQIQESLTT TSTALGKLQD VVNQNAQALN TLVKQLSSNF  960
GAISSVLNDI LSRLDPPEAE VQIDRLITGR LQSLQTYVTQ QLIRAAEIRA SANLAATKMS  1020
ECVLGQSKRV DFCGKGYHLM SFPQAAPHGV VFLHVTYVPS QERNFTTAPA ICHEGKAYFP  1080
REGVFVFNGT SWFITQRNFF SPQIITTDNT FVSGNCDVVI GIINNTVYDP LQPELDSFKE  1140
ELDKYFKNHT SPDVDLGDIS GINASVVNIQ KEIDRLNEVA KNLNESLIDL QELGKYEQYI  1200
KGGGSGYIPE APRDGQAYVR KDGEWVLLST FLGSHHHHHH                       1240

SEQ ID NO: 10           moltype = AA  length = 1267
FEATURE                 Location/Qualifiers
REGION                  1..1267
                        note = SARS-CoV2 Spike ectodomain (C SP) AVI tag;
                         Mutations: furinecleavage, Diproline
source                  1..1267
                        mol_type = protein
                        organism = synthetic construct
SEQUENCE: 10
MEFGLSWLFL VAILKGVQCE VQCVNLTTRT QLPPAYTNSF TRGVYYPDKV FRSSVLHSTQ  60
DLFLPFFSNV TWFHAIHVSG TNGTKRFDNP VLPFNDGVYF ASTEKSNIIR GWIFGTTLDS  120
KTQSLLIVNN ATNVVIKVCE FQFCNDPFLG VYYHKNNKSW MESEFRVYSS ANNCTFEYVS  180
QPFLMDLEGK QGNFKNLREF VFKNIDGYFK IYSKHTPINL VRDLPQGFSA LEPLVDLPIG  240
INITRFQTLL ALHRSYLTPG DSSSGWTAGA AAYYVGYLQP RTFLLKYNEN GTITDAVDCA  300
LDPLSETKCT LKSFTVEKGI YQTSNFRVQP TESIVRFPNI TNLCPFGEVF NATRFASVYA  360
WNRKRISNCV ADYSVLYNSA SFSTFKCYGV SPTKLNDLCF TNVYADSFVI RGDEVRQIAP  420
GQTGKIADYN YKLPDDFTGC VIAWNSNNLD SKVGGNYNYL YRLFRKSNLK PFERDISTEI  480
YQAGSTPCNG VEGFNCYFPL QSYGFQPTNG VGYQPYRVVV LSFELLHAPA TVCGPKKSTN  540
LVKNKCVNFN FNGLTGTGVL TESNKKFLPF QQFGRDIADT TDAVRDPQTL EILDITPCSF  600
GGVSVITPGT NTSNQVAVLY QDVNCTEVPV AIHADQLTPT WRVYSTGSNV FQTRAGCLIG  660
AEHVNNSYEC DIPIGAGICA SYQTQTNSPS GAGSVASQSI IAYTMSLGAE NSVAYSNNSI  720
AIPTNFTISV TTEILPVSMT KTSVDCTMYI CGDSTECSNL LLQYGSFCTQ LNRALTGIAV  780
EQDKNTQEVF AQVKQIYKTP PIKDFGGFNF SQILPDPSKP SKRSFIEDLL FNKVTLADAG  840
```

-continued

```
FIKQYGDCLG DIAARDLICA QKFNGLTVLP PLLTDEMIAQ YTSALLAGTI TSGWTFGAGA  900
ALQIPFAMQM AYRFNGIGVT QNVLYENQKL IANQFNSAIG KIQDSLSSTA SALGKLQDVV  960
NQNAQALNTL VKQLSSNFGA ISSVLNDILS RLDPPEAEVQ IDRLITGRLQ SLQTYVTQQL  1020
IRAAEIRASA NLAATKMSEC VLGQSKRVDF CGKGYHLMSF PQSAPHGVVF LHVTYVPAQE  1080
KNFTTAPAIC HDGKAHFPRE GVFVSNGTHW FVTQRNFYEP QIITTDNTFV SGNCDVVIGI  1140
VNNTVYDPLQ PELDSFKEEL DKYFKNHTSP DVDLGDISGI NASVVNIQKE IDRLNEVAKN  1200
LNESLIDLQE LGKYEQYIKG GGSGYIPEAP RDGQAYVRKD GEWVLLSTFL GSGLNDIFEA  1260
QKIEWHE                                                            1267

SEQ ID NO: 11          moltype = AA  length = 1258
FEATURE                Location/Qualifiers
REGION                 1..1258
                       note = C SP 6 His tag; Mutations: furine cleavage, Diproline
source                 1..1258
                       mol_type = protein
                       organism = synthetic construct
SEQUENCE: 11
MEFGLSWLFL VAILKGVQCE VQCVNLTTRT QLPPAYTNSF TRGVYYPDKV FRSSVLHSTQ  60
DLFLPFFSNV TWFHAIHVSG TNGTKRFDNP VLPFNDGVYF ASTEKSNIIR GWIFGTTLDS  120
KTQSLLIVNN ATNVVIKVCE FQFCNDPFLG VYYHKNNKSW MESEFRVYSS ANNCTFEYVS  180
QPFLMDLEGK QGNFKNLREF VFKNIDGYFK IYSKHTPINL VRDLPQGFSA LEPLVDLPIG  240
INITRFQTLL ALHRSYLTPG DSSSGWTAGA AAYYVGYLQP RTFLLKYNEN GTITDAVDCA  300
LDPLSETKCT LKSFTVEKGI YQTSNFRVQP TESIVRFPNI TNLCPFGEVF NATRFASVYA  360
WNRKRISNCV ADYSVLYNSA SFSTFKCYGV SPTKLNDLCF TNVYADSFVI RGDEVRQIAP  420
GQTGKIADYN YKLPDDFTGC VIAWNSNNLD SKVGGNYNYL YRLFRKSNLK PFERDISTEI  480
YQAGSTPCNG VEGFNCYFPL QSYGFQPTNG VGYQPYRVVV LSFELLHAPA TVCGPKKSTN  540
LVKNKCVNFN FNGLTGTGVL TESNKKFLPF QQFGRDIADT TDAVRDPQTL EILDITPCSF  600
GGVSVITPGT NTSNQVAVLY QDVNCTEVPV AIHADQLTPT WRVYSTGSNV FQTRAGCLIG  660
AEHVNNSYEC DIPIGAGICA SYQTQTNSPS GAGSVASQSI IAYTMSLGAE NSVAYSNNSI  720
AIPTNFTISV TTEILPVSMT KTSVDCTMYI CGDSTECSNL LLQYGSFCTQ LNRALTGIAV  780
EQDKNTQEVF AQVKQIYKTP PIKDFGGFNF SQILPDPSKP SKRSFIEDLL FNKVTLADAG  840
FIKQYGDCLG DIAARDLICA QKFNGLTVLP PLLTDEMIAQ YTSALLAGTI TSGWTFGAGA  900
ALQIPFAMQM AYRFNGIGVT QNVLYENQKL IANQFNSAIG KIQDSLSSTA SALGKLQDVV  960
NQNAQALNTL VKQLSSNFGA ISSVLNDILS RLDPPEAEVQ IDRLITGRLQ SLQTYVTQQL  1020
IRAAEIRASA NLAATKMSEC VLGQSKRVDF CGKGYHLMSF PQSAPHGVVF LHVTYVPAQE  1080
KNFTTAPAIC HDGKAHFPRE GVFVSNGTHW FVTQRNFYEP QIITTDNTFV SGNCDVVIGI  1140
VNNTVYDPLQ PELDSFKEEL DKYFKNHTSP DVDLGDISGI NASVVNIQKE IDRLNEVAKN  1200
LNESLIDLQE LGKYEQYIKG GGSGYIPEAP RDGQAYVRKD GEWVLLSTFL GSHHHHHH    1258

SEQ ID NO: 12          moltype = AA  length = 1336
FEATURE                Location/Qualifiers
REGION                 1..1336
                       note = MERS Spike ectodomain (M SP) 6His tag; Mutations:
                        Furinecleavage, Diproline
source                 1..1336
                       mol_type = protein
                       organism = synthetic construct
SEQUENCE: 12
MEFGLSWLFL VAILKGVQCE VVDVGPDSVK SACIEVDIQQ TFFDKTWPRP IDVSKADGII  60
YPQGRTYSNI TITYQGLFPY QGDHGDMYVY SAGHATGTTP QKLFVANYSQ DVKQFANGFV  120
VRIGAAANST GTVIISPSTS ATIRKIYPAF MLGSSVGNFS DGKMGRFFNH TLVLLPDGCG  180
TLLRAFYCIL EPRSGNHCPA GNSYTSFATY HTPATDCSDG NYNRNASLNS FKEYFNLRNC  240
TFMYTYNITE DEILEWFGIT QTAQGVHLFS SRYVDLYGGN MFQFATLPVY DTIKYYSIIP  300
HSIRSIQSDR KAWAAFYVYK LQPLTFLLDF SVDGYIRRAI DCGFNDLSQL HCSYESFDVE  360
SGVYSVSSFE AKPSGSVVEQ AEGVECDFSP LLSGTPPQVY NFKRLVFTNC NYNLTKLLSL  420
FSVNDFTCSQ ISPAAIASNC YSSLILDYFS YPLSMKSDLS VSSAGPISQF NYKQSFSNPT  480
CLILATVPHN LTTITKPLKY SYINKCSRLL SDDRTEVPQL VNANQYSPCV SIVPSTVWED  540
GDYYRKQLSP LEGGGWLVAS GSTVAMTEQL QMGFGITVQY GTDTNSVCPK LEFANDTKIA  600
SQLGNCVEYS LYGVSGRGVF QNCTAVGVRQ QRFVYDAYQN LVGYYSDDGN YYCLRACVSV  660
PVSVIYDKET KTHATLFGSV ACEHISSTMS QYSRSTRSML KRRDSTYGPL QTPVGCVLGL  720
VNSSLFVEDC KLPLGQSLCA LPDTPSTLTP ASVGSVPGEM RLASIAFNHP IQVDQLNSSY  780
FKLSIPTNFS FGVTQEYIQT TIQKVTVDCK QYVCNGFQKC EQLLREYGQF CSKINQALHG  840
ANLRQDDSVR NLFASVKSSQ SSPIIPGFGG DFNLTLLEPV SISTGSRSAR SAIEDLLFDK  900
VTIADPGYMQ GYDDCMQQGP ASARDLICAQ YVAGYKVLPP LMDVNMEAAY TSSLLGSIAG  960
VGWTAGLSSF AAIPFAQSIF YRLNGVGITQ QVLSENQKLI ANKFNQALGA MQTGFTTTNE  1020
AFQKVQDAVN NNAQALSKLA SELSNTFGAI SASIGDIIQR LDPPEQDAQI DRLINGRLTT  1080
LNAFVAQQLV RSESAALSAQ LAKDKVNECV KAQSKRSGFC GQGTHIVSFV VNAPNGLYFM  1140
HVGYYPSNHI EVVSAYGLCD AANPTNCIAP VNGYFIKTNN TRIVDEWSYT GSSFYAPEPI  1200
TSLNTKYVAP QVTYQNISTN LPPPLLGNST GIDFQDELDE FFKNVSTSIP NFGSLTQINT  1260
TLLDLTYEML SLQQVVKALN ESYIDLKELG NYTYYNKGGG SGYIPEAPRD GQAYVRKDGE  1320
WVLLSTFLGS HHHHHH                                                  1336

SEQ ID NO: 13          moltype = AA  length = 1345
FEATURE                Location/Qualifiers
REGION                 1..1345
                       note = M SP AVI Tag; Mutations: Furine cleavage, Diproline
source                 1..1345
                       mol_type = protein
                       organism = synthetic construct
```

-continued

```
SEQUENCE: 13
MEFGLSWLFL VAILKGVQCE VVDVGPDSVK SACIEVDIQQ TFFDKTWPRP IDVSKADGII  60
YPQGRTYSNI TITYQGLFPY QGDHGDMYVY SAGHATGTTP QKLFVANYSQ DVKQFANGFV  120
VRIGAAANST GTVIISPSTS ATIRKIYPAF MLGSSVGNFS DGKMGRFFNH TLVLLPDGCG  180
TLLRAFYCIL EPRSGNHCPA GNSYTSFATY HTPATDCSDG NYNRNASLNS FKEYFNLRNC  240
TFMYTYNITE DEILEWFGIT QTAQGVHLFS SRYVDLYGGN MFQFATLPVY DTIKYYSIIP  300
HSIRSIQSDR KAWAAFYVYK LQPLTFLLDF SVDGYIRRAI DCGFNDLSQL HCSYESFDVE  360
SGVYSVSSFE AKPSGSVVEQ AEGVECDFSP LLSGTPPQVY NFKRLVFTNC NYNLTKLLSL  420
FSVNDFTCSQ ISPAAIASNC YSSLILDYFS YPLSMKSDLS VSSAGPISQF NYKQSFSNPT  480
CLILATVPHN LTTITKPLKY SYINKCSRLL SDDRTEVPQL VNANQYSPCV SIVPSTVWED  540
GDYYRKQLSP LEGGGWLVAS GSTVAMTEQL QMGFGITVQY GTDTNSVCPK LEFANDTKIA  600
SQLGNCVEYS LYGVSGRGVF QNCTAVGVRQ QRFVYDAYQN LVGYYSDDGN YYCLRACVSV  660
PVSVIYDKET KTHATLFGSV ACEHISSTMS QYSRSTRSML KRRDSTYGPL QTPVGCVLGL  720
VNSSLFVEDC KLPLGQSLCA LPDTPSTLTP ASVGSVPGEM RLASIAFNHP IQVDQLNSSY  780
FKLSIPTNFS FGVTQEYIQT TIQKVTVDCK QYVCNGFQKC EQLLREYGQF CSKINQALHG  840
ANLRQDDSVR NLFASVKSSQ SSPIIPGFGG DFNLTLLEPV SISTGSRSAR SAIEDLLFDK  900
VTIADPGYMQ GYDDCMQQGP ASARDLICAQ YVAGYKVLPP LMDVNMEAAY TSSLLGSIAG  960
VGWTAGLSSF AAIPFAQSIF YRLNGVGITQ QVLSENQKLI ANKFNQALGA MQTGFTTTNE  1020
AFQKVQDAVN NNAQALSKLA SELSNTFGAI SASIGDIIQR LDPPEQDAQI DRLINGRLTT  1080
LNAFVAQQLV RSESAALSAQ LAKDKVNECV KAQSKRSGFC GQGTHIVSFV VNAPNGLYFM  1140
HVGYYPSNHI EVVSAYGLCD AANPTNCIAP VNGYFIKTNN TRIVDEWSYT GSSFYAPEPI  1200
TSLNTKYVAP QVTYQNISTN LPPPLLGNST GIDFQDELDE FFKNVSTSIP NFGSLTQINT  1260
TLLDLTYEML SLQQVVKALN ESYIDLKELG NYTYYNKGGG SGYIPEAPRD GQAYVRKDGE  1320
WVLLSTFLGS GLNDIFEAQK IEWHE                                      1345

SEQ ID NO: 14          moltype = AA  length = 1310
FEATURE                Location/Qualifiers
REGION                 1..1310
                       note = OC43 Spike ectodomain (O SP) 6His tag; Mutations:
                        Furinecleavage, Diproline
source                 1..1310
                       mol_type = protein
                       organism = synthetic construct
SEQUENCE: 14
MEFGLSWLFL VAILKGVQCE VVIGDLKCTS DNINDKDTGP PPISTDTVDV TNGLGTYYVL  60
DRVYLNTTLF LNGYYPTSGS TYRNMALKGS VLLSRLWFKP PFLSDFINGI FAKVKNTKVI  120
KDRVMYSEFP AITIGSTFVN TSYSVVVQPR TINSTQDGDN KLQGLLEVSV CQYNMCEYPQ  180
TICHPNLGNH RKELWHLDTG VVSCLYKRNF TYDVNADYLY FHFYQEGGTF YAYFTDTGVV  240
TKFLFNVYLG MALSHYYVMP LTCNSKLTLE YWVTPLTSRQ YLLAFNQDGI IFNAVDCMSD  300
FMSEIKCKTQ SIAPPTGVYE LNGYTVQPIA DVYRRKPNLP NCNIEAWLND KSVPSPLNWE  360
RKTFSNCNFN MSSLMSFIQA DSFTCNNIDA AKIYGMCFSS ITIDKFAIPN GRKVDLQLGN  420
LGYLQSFNYR IDTTATSCQL YYNLPAANVS VSRFNPSTWN KRFGFIEDSV FKPRPAGVLT  480
NHDVVYAQHC FKAPKNFCPC KLNGSCVGSG PGKNNGIGTC PAGTNYLTCD NLCTPDPITF  540
TGTYKCPQTK SLVGIGEHCS GLAVKSDYCG GNSCTCRPQA FLGWSADSCL QGDKCNIFAN  600
FILHDVNSGL TCSTDLQKAN TDIILGVCVN YDLYGILGQG IFVEVNATYY NSWQNLLYDS  660
NGNLYGFRDY ITNRTFMIRS CYSGRVSAAF HANSSEPALL FRNIKCNYVF NNSLTRQLQP  720
INYFDSYLGC VVNAYNSTAI SVQTCDLTVG SGYCVDYSKN GGSGGAITTG YRFTNFEPFT  780
VNSVNDSLEP VGGLYEIQIP SEFTIGNMVE FIQTSSPKVT IDCAAFVCGD YAACKSQLVE  840
YGSFCDNINA ILTEVNELLD TTQLQVANSL MNGVTLSTKL KDGVNFNVDD INFSPVLGCL  900
GSECSKASSR SAIEDLLFDK VKLSDVGFVE AYNNCTGGAE IRDLICVQSY KGIKVLPPLL  960
SENQFSGYTL AATSASLFPP WTAAAGVPFY LNVQYRINGL GVTMDVLSQN QKLIANAFNN  1020
ALYAIQEGFD ATNSALVKIQ AVVNANAEAL NNLLQQLSNR FGAISASLQE ILSRLDALEA  1080
EAQIDRLING RLTALNAYVS QQLSDSTLVK FSAAQAMEKV NECVKSQSSR INFCGNGNHI  1140
ISLVQNAPYG LYFIHFSYVP TKYVTARVSP GLCIAGDRGI APKSGYFVNV NNTWMYTGSG  1200
YYYPEPITEN NVVVMSTCAV NYTKAPYVML NTSIPNLPDF KEELDQWFKN QTSVAPDLSL  1260
DYINVTFLDL LGGGSGYIPE APRDGQAYVR KDGEWVLLST FLGSHHHHHH            1310

SEQ ID NO: 15          moltype = AA  length = 1319
FEATURE                Location/Qualifiers
REGION                 1..1319
                       note = O SP AVI tag; Mutations: Furine cleavage, Diproline
source                 1..1319
                       mol_type = protein
                       organism = synthetic construct
SEQUENCE: 15
MEFGLSWLFL VAILKGVQCE VVIGDLKCTS DNINDKDTGP PPISTDTVDV TNGLGTYYVL  60
DRVYLNTTLF LNGYYPTSGS TYRNMALKGS VLLSRLWFKP PFLSDFINGI FAKVKNTKVI  120
KDRVMYSEFP AITIGSTFVN TSYSVVVQPR TINSTQDGDN KLQGLLEVSV CQYNMCEYPQ  180
TICHPNLGNH RKELWHLDTG VVSCLYKRNF TYDVNADYLY FHFYQEGGTF YAYFTDTGVV  240
TKFLFNVYLG MALSHYYVMP LTCNSKLTLE YWVTPLTSRQ YLLAFNQDGI IFNAVDCMSD  300
FMSEIKCKTQ SIAPPTGVYE LNGYTVQPIA DVYRRKPNLP NCNIEAWLND KSVPSPLNWE  360
RKTFSNCNFN MSSLMSFIQA DSFTCNNIDA AKIYGMCFSS ITIDKFAIPN GRKVDLQLGN  420
LGYLQSFNYR IDTTATSCQL YYNLPAANVS VSRFNPSTWN KRFGFIEDSV FKPRPAGVLT  480
NHDVVYAQHC FKAPKNFCPC KLNGSCVGSG PGKNNGIGTC PAGTNYLTCD NLCTPDPITF  540
TGTYKCPQTK SLVGIGEHCS GLAVKSDYCG GNSCTCRPQA FLGWSADSCL QGDKCNIFAN  600
FILHDVNSGL TCSTDLQKAN TDIILGVCVN YDLYGILGQG IFVEVNATYY NSWQNLLYDS  660
NGNLYGFRDY ITNRTFMIRS CYSGRVSAAF HANSSEPALL FRNIKCNYVF NNSLTRQLQP  720
INYFDSYLGC VVNAYNSTAI SVQTCDLTVG SGYCVDYSKN GGSGGAITTG YRFTNFEPFT  780
VNSVNDSLEP VGGLYEIQIP SEFTIGNMVE FIQTSSPKVT IDCAAFVCGD YAACKSQLVE  840
```

-continued

```
YGSFCDNINA ILTEVNELLD TTQLQVANSL MNGVTLSTKL KDGVNFNVDD INFSPVLGCL  900
GSECSKASSR SAIEDLLFDK VKLSDVGFVE AYNNCTGGAE IRDLICVQSY KGIKVLPPLL  960
SENQFSGYTL AATSASLFPP WTAAAGVPFY LNVQYRINGL GVTMDVLSQN QKLIANAFNN  1020
ALYAIQEGFD ATNSALVKIQ AVVNANAEAL NNLLQQLSNR FGAISASLQE ILSRLDALEA  1080
EAQIDRLING RLTALNAYVS QQLSDSTLVK FSAAQAMEKV NECVKSQSSR INFCGNGNHI  1140
ISLVQNAPYG LYFIHFSYVP TKYVTARVSP GLCIAGDRGI APKSGYFVNV NNTWMYTGSG  1200
YYYPEPITEN NVVVMSTCAV NYTKAPYVML NTSIPNLPDF KEELDQWFKN QTSVAPDLSL  1260
DYINVTFLDL LGGGSGYIPE APRDGQAYVR KDGEWVLLST FLGSGLNDIF EAQKIEWHE   1319

SEQ ID NO: 16          moltype = AA  length = 1328
FEATURE                Location/Qualifiers
REGION                 1..1328
                       note = HKU1 Spike ectodomain (H SP) 6His tag; Mutations:
                        Furinecleavage, Diproline
source                 1..1328
                       mol_type = protein
                       organism = synthetic construct
SEQUENCE: 16
MEFGLSWLFL VAILKGVQCE VVIGDFNCTN FAINDLNTTV PRISEYVVDV SYGLGTYYIL  60
DRVYLNTTIL FTGYFPKSGA NFRDLSLKGT TYLSTLWYQK PFLSDFNNGI FSRVKNTKLY  120
VNKTLYSEFS TIVIGSVFIN NSYTIVVQPH NGVLEITACQ YTMCEYPHTI CKSKGSSRNE  180
SWHFDKSEPL CLFKKNFTYN VSTDWLYFHF YQERGTFYAY YADSGMPTTF LFSLYLGTLL  240
SHYYVLPLTC NAISSNTDNE TLQYWVTPLS KRQYLLKFDN RGVITNAVDC SSSFFSEIQC  300
KTKSLLPNTG VYDLSGFTVK PVATVHRRIP DLPDCDIDKW LNNFNVPSPL NWERKIFSNC  360
NFNLSTLLRL VHTDSFSCNN FDESKIYGSC FKSIVLDKFA IPNSRRSDLQ LGSSGFLQSS  420
NYKIDTTSSS CQLYYSLPAI NVTINNYNPS SWNRRYGFNN FNLSSHSVVY SRYCFSVNNT  480
FCPCAKPSFA SSCKSHKPPS ASCPIGTNYR SCESTTVLDH TDWCRCSCLP DPITAYDPRS  540
CSQKKSLVGV GEHCAGFGVD EEKCGVLDGS YNVSCLCSTD AFLGWSYDTC VSNNRCNIFS  600
NFILNGINSG TTCSNDLLQP NTEVFTDVCV DYDLYGITGQ GIFKEVSAVY YNSWQNLLYD  660
SNGNIIGFKD FVTNKTYNIF PCYAGRVSAA FHQNASSLAL LYRNLKCSYV LNNISLTTQP  720
YFDSYLGCVF NADNLTDYSV SSCALRMGSG FCVDYNSPSS SSSGGSGSSI SASYRFVTFE  780
PFNVSFVNDS IESVGGLYEI KIPTNFTIVG QEEFIQTNSP KVTIDCSLFV CSNYAACHDL  840
LSEYGTFCDN INSILDEVNG LLDTTQLHVA DTLMQGVTLS SNLNTNLHFD VDNINFKSLV  900
GCLGPHCGSS SRSFFEDLLF DKVKLSDVGF VEAYNNCTGG SEIRDLLCVQ SFNGIKVLPP  960
ILSESQISGY TTAATVAAMF PPWSAAAGIP FSLNVQYRIN GLGVTMDVLN KNQKLIATAF  1020
NNALLSIQNG FSATNSALAK IQSVVNSNAQ ALNSLLQQLF NKFGAISSSL QEILSRLDAL  1080
EAQVQIDRLI NGRLTALNAY VSQQLSDISL VKFGAALAME KVNECVKSQS PRINFCGNGN  1140
HILSLVQNAP YGLLFMHFSY KPISFKTVLV SPGLCISGDV GIAPKQGYFI KHNDHWMFTG  1200
SSYYYPEPIS DKNVVFMNTC SVNFTKAPLV YLNHSVPKLS DFESELSHWF KNQTSIAPNL  1260
TLNLHTINAT FLDLYYEMNL IQESIKSLNG GGSGYIPEAP RDGQAYVRKD GEWVLLSTFL  1320
GSHHHHHH                                                         1328

SEQ ID NO: 17          moltype = AA  length = 1337
FEATURE                Location/Qualifiers
REGION                 1..1337
                       note = H SP Avi Tag; Mutations: Furine cleavage, Diproline
source                 1..1337
                       mol_type = protein
                       organism = synthetic construct
SEQUENCE: 17
MEFGLSWLFL VAILKGVQCE VVIGDFNCTN FAINDLNTTV PRISEYVVDV SYGLGTYYIL  60
DRVYLNTTIL FTGYFPKSGA NFRDLSLKGT TYLSTLWYQK PFLSDFNNGI FSRVKNTKLY  120
VNKTLYSEFS TIVIGSVFIN NSYTIVVQPH NGVLEITACQ YTMCEYPHTI CKSKGSSRNE  180
SWHFDKSEPL CLFKKNFTYN VSTDWLYFHF YQERGTFYAY YADSGMPTTF LFSLYLGTLL  240
SHYYVLPLTC NAISSNTDNE TLQYWVTPLS KRQYLLKFDN RGVITNAVDC SSSFFSEIQC  300
KTKSLLPNTG VYDLSGFTVK PVATVHRRIP DLPDCDIDKW LNNFNVPSPL NWERKIFSNC  360
NFNLSTLLRL VHTDSFSCNN FDESKIYGSC FKSIVLDKFA IPNSRRSDLQ LGSSGFLQSS  420
NYKIDTTSSS CQLYYSLPAI NVTINNYNPS SWNRRYGFNN FNLSSHSVVY SRYCFSVNNT  480
FCPCAKPSFA SSCKSHKPPS ASCPIGTNYR SCESTTVLDH TDWCRCSCLP DPITAYDPRS  540
CSQKKSLVGV GEHCAGFGVD EEKCGVLDGS YNVSCLCSTD AFLGWSYDTC VSNNRCNIFS  600
NFILNGINSG TTCSNDLLQP NTEVFTDVCV DYDLYGITGQ GIFKEVSAVY YNSWQNLLYD  660
SNGNIIGFKD FVTNKTYNIF PCYAGRVSAA FHQNASSLAL LYRNLKCSYV LNNISLTTQP  720
YFDSYLGCVF NADNLTDYSV SSCALRMGSG FCVDYNSPSS SSSGGSGSSI SASYRFVTFE  780
PFNVSFVNDS IESVGGLYEI KIPTNFTIVG QEEFIQTNSP KVTIDCSLFV CSNYAACHDL  840
LSEYGTFCDN INSILDEVNG LLDTTQLHVA DTLMQGVTLS SNLNTNLHFD VDNINFKSLV  900
GCLGPHCGSS SRSFFEDLLF DKVKLSDVGF VEAYNNCTGG SEIRDLLCVQ SFNGIKVLPP  960
ILSESQISGY TTAATVAAMF PPWSAAAGIP FSLNVQYRIN GLGVTMDVLN KNQKLIATAF  1020
NNALLSIQNG FSATNSALAK IQSVVNSNAQ ALNSLLQQLF NKFGAISSSL QEILSRLDAL  1080
EAQVQIDRLI NGRLTALNAY VSQQLSDISL VKFGAALAME KVNECVKSQS PRINFCGNGN  1140
HILSLVQNAP YGLLFMHFSY KPISFKTVLV SPGLCISGDV GIAPKQGYFI KHNDHWMFTG  1200
SSYYYPEPIS DKNVVFMNTC SVNFTKAPLV YLNHSVPKLS DFESELSHWF KNQTSIAPNL  1260
TLNLHTINAT FLDLYYEMNL IQESIKSLNG GGSGYIPEAP RDGQAYVRKD GEWVLLSTFL  1320
GSGLNDIFEA QKIEWHE                                               1337

SEQ ID NO: 18          moltype = AA  length = 266
FEATURE                Location/Qualifiers
REGION                 1..266
                       note = Sars-CoV-2 receptor binding domain (C RBD) 6HIS AVI
                        tag
```

```
source                  1..266
                        mol_type = protein
                        organism = synthetic construct
SEQUENCE: 18
MEFGLSWLFL VAILKGVQCE VRVQPTESIV RFPNITNLCP FGEVFNATRF ASVYAWNRKR  60
ISNCVADYSV LYNSASFSTF KCYGVSPTKL NDLCFTNVYA DSFVIRGDEV RQIAPGQTGK  120
IADYNYKLPD DFTGCVIAWN SNNLDSKVGG NYNYLYRLFR KSNLKPFERD ISTEIYQAGS  180
TPCNGVEGFN CYFPLQSYGF QPTNGVGYQP YRVVVLSFEL LHAPATVCGP KKSTNLVKNK  240
CVNFGGLNDI FEAQKIEWHE HHHHHH                                      266

SEQ ID NO: 19           moltype = AA  length = 335
FEATURE                 Location/Qualifiers
REGION                  1..335
                        note = Sars-CoV-2 N-terminal domain (C NTD)
source                  1..335
                        mol_type = protein
                        organism = synthetic construct
SEQUENCE: 19
MEFGLSWLFL VAILKGVQCE VQCVNLTTRT QLPPAYTNSF TRGVYYPDKV FRSSVLHSTQ  60
DLFLPFFSNV TWFHAIHVSG TNGTKRFDNP VLPFNDGVYF ASTEKSNIIR GWIFGTTLDS  120
KTQSLLIVNN ATNVVIKVCE FQFCNDPFLG VYYHKNNKSW MESEFRVYSS ANNCTFEYVS  180
QPFLMDLEGK QGNFKNLREF VFKNIDGYFK IYSKHTPINL VRDLPQGFSA LEPLVDLPIG  240
INITRFQTLL ALHRSYLTPG DSSSGWTAGA AAYYVGYLQP RTFLLKYNEN GTITDAVDCA  300
LDPLSETKCT LKSGGLNDIF EAQKIEWHEH HHHHH                            335

SEQ ID NO: 20           moltype = AA  length = 265
FEATURE                 Location/Qualifiers
REGION                  1..265
                        note = SARS1-CoV Receptor binding domain (S RBD) 6HIS AVI
                         tag
source                  1..265
                        mol_type = protein
                        organism = synthetic construct
SEQUENCE: 20
MEFGLSWLFL VAILKGVQCE VRVVPSGDVV RFPNITNLCP FGEVFNATKF PSVYAWERKK  60
ISNCVADYSV LYNSTFFSTF KCYGVSATKL NDLCFSNVYA DSFVVKGDDV RQIAPGQTGV  120
IADYNYKLPD DFMGCVLAWN TRNIDATSTG NYNYKYRYLR HGKLRPFERD ISNVPFSPDG  180
KPCTPPALNC YWPLNDYGFY TTTGIGYQPY RVVVLSFELL NAPATVCGPK LSTDLIKNQC  240
VNFGGLNDIF EAQKIEWHEH HHHHH                                       265

SEQ ID NO: 21           moltype = AA  length = 446
FEATURE                 Location/Qualifiers
REGION                  1..446
                        note = SARS-CoV Nucleocapsid protein (S NP) 6HIS AVI tag
source                  1..446
                        mol_type = protein
                        organism = synthetic construct
SEQUENCE: 21
MSDNGPQSNQ RSAPRITFGG PTDSTDNNQN GGRNGARPKQ RRPQGLPNNT ASWFTALTQH  60
GKEELRFPRG QGVPINTNSG PDDQIGYYRR ATRRVRGGDG KMKELSPRWY FYYLGTGPEA  120
SLPYGANKEG IVWVATEGAL NTPKDHIGTR NPNNNAATVL QLPQGTTLPK GFYAEGSRGG  180
SQASSRSSSR SRGNSRNSTP GSSRGNSPAR MASGGGETAL ALLLLDRLNQ LESKVSGKGQ  240
QQQGQTVTKK SAAEASKKPR QKRTATKQYN VTQAFGRRGP EQTQGNFGDQ DLIRQGTDYK  300
HWPQIAQFAP SASAFFGMSR IGMEVTPSGT WLTYHGAIKL DDKDPQFKDN VILLNKHIDA  360
YKTFPPTEPK KDKKKKTDEA QPLPQRQKKQ PTVTLLPAAD MDDFSRQLQN SMSGASADST  420
QAGGLNDIFE AQKIEWHELE HHHHHH                                      446

SEQ ID NO: 22           moltype = AA  length = 443
FEATURE                 Location/Qualifiers
REGION                  1..443
                        note = SARS-CoV-2 Nucleocapsid protein (C NP) 6HIS AVI tag
source                  1..443
                        mol_type = protein
                        organism = synthetic construct
SEQUENCE: 22
MSDNGPQNQR NAPRITFGGP SDSTGSNQNG ERSGARSKQR RPQGLPNNTA SWFTALTQHG  60
KEDLKFPRGQ GVPINTNSSP DDQIGYYRRA TRRIRGGDGK MKDLSPRWYF YYLGTGPEAG  120
LPYGANKDGI IWVATEGALN TPKDHIGTRN PANNAAIVLQ LPQGTTLPKG FYAEGSRGGS  180
QASSRSSSRS RNSSRNSTPG SSRGTSPARM AGNGGDAALA LLLLDRLNQL ESKMSGKGQQ  240
QQGQTVTKKS AAEASKKPRQ KRTATKAYNV TQAFGRRGPE QTQGNFGDQE LIRQGTDYKH  300
WPQIAQFAPS ASAFFGMSRI GMEVTPSGTW LTYTGAIKLD DKDPNFKDQV ILLNKHIDAY  360
KTFPPTEPKK DKKKKADETQ ALPQRQKKQQ TVTLLPAADL DDFSKQLQQS MSSADSTQAG  420
GLNDIFEAQK IEWHELEHHH HHH                                         443

SEQ ID NO: 23           moltype = AA  length = 435
FEATURE                 Location/Qualifiers
REGION                  1..435
                        note = MERS Nucleocapsid protein (M NP) 6HIS AVI tag
source                  1..435
```

-continued

```
                         mol_type = protein
                         organism = synthetic construct
SEQUENCE: 23
MASPAAPRAV SFADNNDITN TNLSRGRGRN PKPRAAPNNT VSWYTGLTQH GKVPLTFPPG  60
QGVPLNANST PAQNAGYWRR QDRKINTGNG IKQLAPRWYF YYTGTGPEAA LPFRAVKDGI  120
VWVHEDGATD APSTFGTRNP NNDSAIVTQF APGTKLPKNF HIEGTGGNSQ SSSRASSLSR  180
NSSRSSSQGS RSGNSTRGTS PGPSGIGAVG GDLLYLDLLN RLQALESGKV KQSQPKVITK  240
KDAAAAKNKM RHKRTSTKSF NMVQAFGLRG PGDLQGNFGD LQLNKLGTED PRWPQIAELA  300
PTASAFMGMS QFKLTHQNND DHGNPVYFLR YSGAIKLDPK NPNYNKWLEL LEQNIDAYKT  360
FPKKEKKQKA PKEESTDQMS EPPKEQRVQG SITQRTRTRP SVQPGPMIDV NTDGGLNDIF  420
EAQKIEWHEH HHHHH                                                  435

SEQ ID NO: 24            moltype = AA  length = 470
FEATURE                  Location/Qualifiers
REGION                   1..470
                         note = OC43 Nucleocapsid protein (O NP) 6HIS AVI tag
source                   1..470
                         mol_type = protein
                         organism = synthetic construct
SEQUENCE: 24
MSFTPGKQSS SRASSGNRSG NGILKWADQS DQFRNFQTRG RRAQPKQTAT SQQPSGGNVV  60
PHYSWFSGIT QFQKGKEFEF AEGQGVPIAP GVPATEAKGY WYRHNRRSFK TADGNQRQLL  120
PRWYFYYLGT GPHAKDQYGT DINGVYWVAS NQADVNTPAD IVDRDPSSDE AIPTRFPPGT  180
VLPQGYYIEG SGRSAPNSRS TSRTSSRASS AGSRSRANSG NRTPTSGVTP DMADQIASLV  240
LAKLGKDATK PQQVTKHTAK EVRQKILNKP RQKRSPNKQC TVQQCFGKRG PNQNFGGGEM  300
LKLGTSDPQF PILAELAPTA GAFFFGSKLE LAKVQNLSGN PDEPQKDVYE LRYNGAIRFD  360
STLSGFETIM KVLSENLNAY QQQDGMMNMS PKPQRQRGHK NGQGENDNIS VAVPKSRVQQ  420
NKSIELTAED ISLLKKMDEP FTEDTSEIGG LNDIFEAQKI EWHEHHHHHH             470

SEQ ID NO: 25            moltype = AA  length = 463
FEATURE                  Location/Qualifiers
REGION                   1..463
                         note = HKU1 Nucleocapsid protein (H NP) 6HIS AVI tag
source                   1..463
                         mol_type = protein
                         organism = synthetic construct
SEQUENCE: 25
MSYTPGHYAG SRSSSGNRSG ILKKTSWADQ SERNYQTFNR GRKTQPKFTV STQPQGNTIP  60
HYSWFSGITQ FQKGRDFKFS DGQGVPIAFG VPPSEAKGYW YRHSRRSFKT ADGQQKQLLP  120
RWYFYYLGTG PYANASYGES LEGVFWVANH QADTSTPSDV SSRDPTTQEA IPTRFPPGTI  180
LPQGYYVEGS GRSASNSRPG SRSQSRGPNN RSLSRSNSNF RHSDSIVKPD MADEIANLVL  240
AKLGKDSKPQ QVTKQNAKEI RHKILTKPRQ KRTPNKHCNV QQCFGKRGPS QNFGNAEMLK  300
LGTNDPQFPI LAELAPTPGA FFFGSKLDLV KRDSEADSPV KDVFELHYSG SIRFDSTLPG  360
FETIMKVLEE NLNAYVNSNQ NTDSDSLSSK PQRKRGVKQL PEQFDSLNLS AGTQHISNDF  420
TPEDHSLLAT LDDPYVEDSV AGGLNDIFEA QKIEWHEHHH HHH                   463

SEQ ID NO: 26            moltype = AA  length = 569
FEATURE                  Location/Qualifiers
REGION                   1..569
                         note = Influenza Hemagglutinin:California_VRDL7_2009 H1N1
                          HA (CA09) 6Histag
source                   1..569
                         mol_type = protein
                         organism = synthetic construct
SEQUENCE: 26
MGSLQPLATL YLLGMLVASC LGRLDTLCIG YHANNSTDTV DTVLEKNVTV THSVNLLEDK  60
HNGKLCKLRG VAPLHLGKCN IAGWILGNPE CESLSTASSW SYIVETSSSD NGTCYPGDFI  120
DYEELREQLS SVSSFERFEI FPKTSSWPNH DSNKGVTAAC PHAGAKSFYK NLIWLVKKGN  180
SYPKLSKSYI NDKGKEVLVL WGIHHPPTSA DQQSLYQNAD AYVFVGTSRY SKKFKPEIAI  240
RPKVRGQEGR MNYYWTLVEP GDKITFEATG NLVVPRYAFA MERNAGSGII ISDTPVHDCN  300
TTCQTPKGAI NTSLPFQNIH PITIGKCPKY VKSTKLRLAT GLRNVPSIQS RGLFGAIAGF  360
IEGGWTGMVD GWYGYHHQNE QGSGYAADLK STQNAIDEIT NKVNSVIEKM NTQFTAVGKE  420
FNHLEKRIEN LNKKVDDGFL DIWTYNAELL VLLENERTLD YHDSNVKNLY EKVRSQLKNN  480
AKEIGNGCFE FYHKCDNTCM ESVKNGTYDY PKYSEEAKLN REEIDGVKLE SKRMKQIEDK  540
IEEIESKQKK IENEIARIKK GGGHHHHHH                                   569
```